(12) United States Patent
Ojiri et al.

(10) Patent No.: US 9,090,547 B2
(45) Date of Patent: Jul. 28, 2015

(54) METHOD FOR PRODUCING TRISPHENOLS AND MONOESTER-SUBSTITUTED PRODUCTS THEREOF, AND 4-ACYLARALKYLPHENOL DERIVATIVES

(75) Inventors: Akihiko Ojiri, Wakayama (JP); Takafumi Tsujigami, Wakayama (JP); Kouichi Tanba, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 287 days.

(21) Appl. No.: 13/321,535

(22) PCT Filed: May 19, 2010

(86) PCT No.: PCT/JP2010/058476
§ 371 (c)(1),
(2), (4) Date: Jan. 13, 2012

(87) PCT Pub. No.: WO2010/134559
PCT Pub. Date: Nov. 25, 2010

(65) Prior Publication Data
US 2012/0108853 A1    May 3, 2012

(30) Foreign Application Priority Data

May 19, 2009   (JP) ................ 2009-121169
May 19, 2009   (JP) ................ 2009-121170

(51) Int. Cl.
| | |
|---|---|
| C07C 39/04 | (2006.01) |
| C07C 49/82 | (2006.01) |
| C07C 37/055 | (2006.01) |
| C07C 37/20 | (2006.01) |
| C07C 45/45 | (2006.01) |
| C07C 45/67 | (2006.01) |
| C07C 49/83 | (2006.01) |
| C07C 67/08 | (2006.01) |
| C07C 67/14 | (2006.01) |
| C07C 67/29 | (2006.01) |
| C07C 69/017 | (2006.01) |
| C07C 69/157 | (2006.01) |

(52) U.S. Cl.
CPC ............ *C07C 49/82* (2013.01); *C07C 37/0555* (2013.01); *C07C 37/20* (2013.01); *C07C 45/455* (2013.01); *C07C 45/673* (2013.01); *C07C 49/83* (2013.01); *C07C 67/08* (2013.01); *C07C 67/14* (2013.01); *C07C 67/29* (2013.01); *C07C 69/017* (2013.01); *C07C 69/157* (2013.01)

(58) Field of Classification Search
CPC ...................................................... C07C 39/04
USPC ............................................................ 568/720
See application file for complete search history.

(56) References Cited

U.S. PATENT DOCUMENTS

| | | | | |
|---|---|---|---|---|
| 5,969,167 | A | * | 10/1999 | Sivaram et al. ............. 552/115 |
| 2007/0232839 | A1 | | 10/2007 | Yoshitomo et al. |
| 2009/0232879 | A1 | | 9/2009 | Cable et al. |

FOREIGN PATENT DOCUMENTS

| | | |
|---|---|---|
| JP | 62-084035 A | 4/1987 |
| JP | 63-130565 | 6/1988 |
| JP | 06-032756 A | 2/1994 |
| JP | 06-199719 A | 7/1994 |
| JP | 07-138200 A | 5/1995 |
| JP | 11-049714 A | 2/1999 |
| JP | 2007-326847 A | 12/2007 |

(Continued)

OTHER PUBLICATIONS

Fujimoto, K. et al., Materials Science & Engineering C: Biomimetic and Supramolecular Systems 2007, vol. 27, No. 1, p. 142-147.*

(Continued)

*Primary Examiner* — Yong Chu
*Assistant Examiner* — Sonya Wright
(74) *Attorney, Agent, or Firm* — Knobbe, Martens, Olson & Bear LLP

(57) ABSTRACT

Trisphenols of general formula (1), which are useful as starting materials for polymer, are industrially easily produced by a method using as a starting material 4-aralkylphenol derivatives expressed by general formula (2):

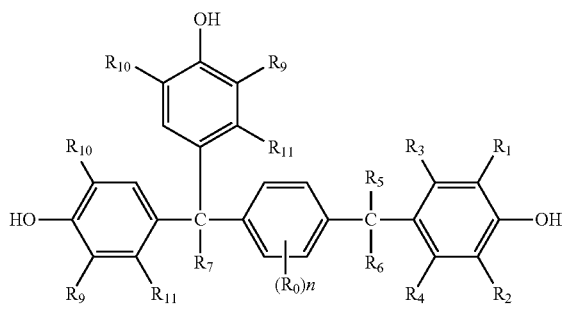

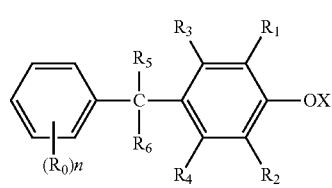

wherein X represents a hydrogen atom or leaving group that can be substituted with a hydrogen atom.

6 Claims, No Drawings

(56) References Cited

FOREIGN PATENT DOCUMENTS

| JP | 2008-191413 A | 8/2008 |
|----|---------------|--------|
| JP | 2008-542301 A1 | 11/2008 |
| WO | WO 2006/128058 A2 | 11/2006 |

OTHER PUBLICATIONS

Kazuhisa Fujimoto et al., "Synthesis and molecular recognition properties of a self-assembling molecule consisted of a porphyrin core and two hydrogen-bonding moieties," Materials Science & Engineering, C: Biomimetic and Supramolecular Systems, 2007, vol. 27, No. 1, p. 142-147.

Notice of reasons for refusal mailed by Japan Patent Office on Jul. 5, 2014 in the corresponding Japanese patent application No. 2011-514441—3 pages.

Bulletin des Societes Chimiques Belges, 1932, 41, pp. 337-348.

CA Database (CAS No. 1081543-60-3, Dec. 8, 2008).

CA Database (CAS No. 149227-30-5, Aug. 11, 1993).

\* cited by examiner

METHOD FOR PRODUCING TRISPHENOLS AND MONOESTER-SUBSTITUTED PRODUCTS THEREOF, AND 4-ACYLARALKYLPHENOL DERIVATIVES

This application is the U.S. National Phase under 35 U.S.C. §371 of International Application PCT/JP2010/058476, filed May 19, 2010, which claims priority to Japanese Patent Application Nos. 2009-121169, filed May 19, 2009 and 2009-121170, filed May 19, 2009. The International Application was published under PCT Article 21(2) in a language other than English.

TECHNICAL FIELD

The present invention relates to a method for producing with ease at high yield and high purity in industrial settings trisphenols, which are useful as materials for polymer compounds such as epoxy resins, polycarbonate resins or the like or as materials or additives for photoresists. It also relates to a new 4-acylaralkylphenol derivative having a bisphenyl molecular skeleton with the acyl group in one phenyl ring and the hydroxyl group or acyloxy group in the other phenyl ring. Such compound is useful as various reactive materials having the effect of improving heat resistance, etc., especially as intermediate materials for generating trisphenols used as materials for polymer compounds such as polycarbonate resins or the like or as materials for photoresists, etc., through reaction with phenols.

Among trisphenols, especially trisphenols other than of the trisphenol methane type, 1-[1,1-bis(4-hydroxyphenyl)ethyl]-4-[1-methyl-1-(4-hydroxyphenyl)ethyl]benzene is known. These trisphenols are favorably used as materials for polymer compounds such as epoxy resins, polycarbonate resins or the like or as materials or additives for photoresists, etc. These trisphenols are known to be obtained by reacting isopropenylacetophenone and phenols (Patent Literature 1).

However, this known material isopropenylacetophenone presents a problem in that it contains active olefin groups and thus has poor storage stability, and easily forms a polymer by readily undergoing polymerization due to heat or impurities such as acid or the like are mixed in. Other problems of isopropenylacetophenone include high cost and low yield of synthesis.

Accordingly, there is a need for a method for producing trisphenols with ease and at high efficiency in industrial settings without using alkenyl acetophenones such as isopropenylacetophenone or the like as the materials, but using an readily available material offering high storage stability, as well as a need for a material compound that can be reacted with phenols to produce trisphenols.

PRIOR ART LITERATURE

Patent Literature

Patent Literature 1: Japanese Patent Laid-open No. Sho 62-084035

SUMMARY OF THE INVENTION

Problems to Be Solved by the Invention

The present invention was developed to solve the aforementioned problems associated with the producing of trisphenols, and it is an object of the present invention to provide a method for producing trisphenols at high yield and high purity through reaction conditions that can be implemented easily in industrial settings, without using alkenylacetophenones as the starting materials, but using a material that offers excellent storage stability and can be obtained easily in industrial settings. It is a further object of the present invention to provide a method for producing monoester-substituted trisphenols, which are useful as intermediate materials of trisphenols, reactive monomer, etc., that can be easily converted into trisphenols by eliminating the leaving group, and to provide a compound that can be reacted with phenols to generate trisphenols or compound that itself can be utilized as various reactive compounds.

Means for Solving the Problems

After studying in earnest for ways to achieve the aforementioned objects, the inventors completed the present invention by finding ways to achieve the aforementioned objects, as follows: For example, use, as the starting material, 4-aralkylphenol derivatives according to general formula (2) below that can be easily obtained by a known method using a readily available material, such as reacting phenols with styrenes or 1-hydroxyalkylbenzenes, etc., and selectively nucleus-acylate the para-position of the phenyl nucleus of the aralkyl group constituting the 4-aralkylphenols to obtain 4-acylaralkylphenol derivatives, after which the leaving group of the obtained 4-acylaralkylphenol derivatives is substituted with a hydrogen atom to obtain 4-acylaralkylphenols, and then cause the 4-acylaralkylphenols to undergo condensation reaction with phenols in the presence of an acid catalyst, or cause the 4-acylaralkylphenol derivatives to undergo condensation reaction with phenols in the presence of an acid catalyst, followed by substituting the leaving group of the obtained trisphenol derivatives with a hydrogen atom, to obtain the target trisphenols.

In addition, the inventors found a 4-acylaralkylphenol derivative having a bisphenyl molecular skeleton with the acyl group at the para-position in one phenyl ring and the hydroxyl group or acyloxy group at the para-position in the other phenyl ring. By realizing that such compound was new and would easily generate a trisphenol when reacted with a phenol, or reacted with a phenol and the resulting acyloxy group was hydrolyzed, and that this compound itself had two highly reactive function groups at both ends of the bisphenyl skeletal molecule so it can be used as various reaction intermediates, the inventors completed the present invention.

In other words, the present invention provides a method for producing trisphenols expressed by general formula (1)

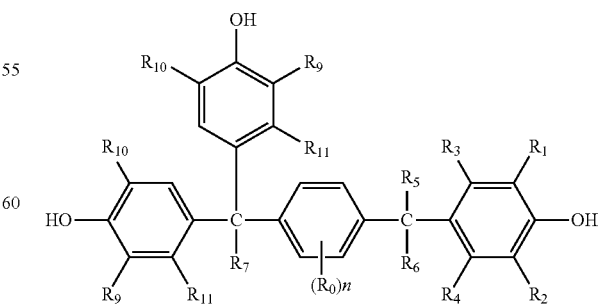

(1)

(in the formula, $R_1$ to $R_4$ each independently represent a hydrogen atom, alkyl group, alkoxyl group, aromatic hydrocarbon group, halogen atom, acyloxy group or hydroxyl group; $R_5$ and $R_6$ each independently represent a hydrogen atom or alkyl group; $R_7$ represents a hydrogen atom or alkyl group; $R_0$ represents an alkyl group, alkoxyl group or halogen atom; n is 0 or an integer of 1 to 4, where if n is 2 or greater, all $R_0$'s may be the same or different; and $R_9$ to $R_{11}$ each independently represent a hydrogen atom, alkyl group, alkoxyl group, aromatic hydrocarbon group, halogen atom or hydroxyl group), wherein the producing method is characterized by using as the starting material 4-aralkylphenol derivatives expressed by general formula (2)

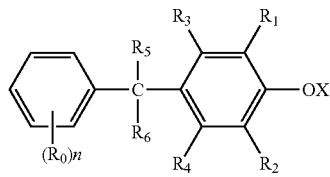

(2)

(in the formula, $R_1$ to $R_4$, $R_5$ and $R_6$, and $R_0$ and n are the same as the corresponding items in general formula (1), while X represents a hydrogen atom or leaving group that can be substituted with a hydrogen atom, where if n is 1 or greater, $R_0$ is not substituted at the 4-position of the phenyl group).

Also, a method for producing trisphenols according to an embodiment of the present invention, wherein X in general formula (2) is a leaving group that can be substituted with a hydrogen atom and this leaving group (hereinafter sometimes referred to as "Xa") is an acyl group, is a favorable embodiment of the present invention.

In addition, a method for producing trisphenols according to an embodiment of the present invention, characterized by comprising a nucleus-acylation process (A) as well as subsequent phenols condensation process (B) and elimination process (C) for substituting Xa with a hydrogen atom, is a favorable embodiment of the present invention.

Process (A): Nucleus-acylate the 4-aralkylphenol derivatives expressed by general formula (2) above to obtain 4-acylaralkylphenol derivatives expressed by general formula (3)

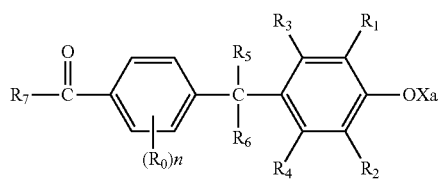

(3)

(in the formula, $R_1$ to $R_4$, $R_5$ and $R_6$, and $R_0$ and n are the same as the corresponding items in general formula (2), while $R_7$ is the same as the corresponding item in general formula (1) and Xa represents a leaving group that can be substituted with a hydrogen atom).

Process (B): Cause phenols expressed by general formula (4)

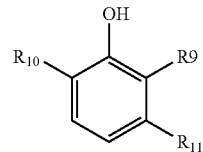

(4)

(in the formula, $R_9$ to $R_{11}$ are the same as the corresponding items in general formula (1))

to undergo condensation reaction with the 4-acylaralkylphenol derivatives expressed by general formula (3) above as obtained by process (A), to obtain trisphenol derivatives expressed by general formula (5)

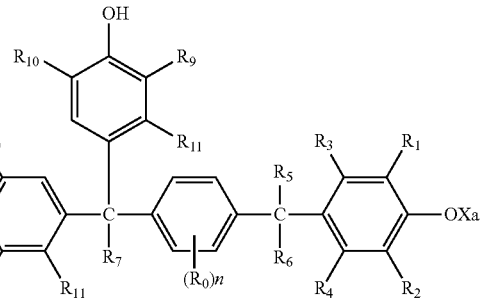

(5)

(in the formula, $R_1$ to $R_4$, $R_5$ and $R_6$, $R_0$ and n, $R_7$, and $R_9$ to $R_{11}$ are the same as the corresponding items in general formula (1), while Xa represents a leaving group that can be substituted with a hydrogen atom)

or, cause the aforementioned phenols to undergo condensation reaction with the 4-acylaralkylphenols expressed by general formula (6) as obtained by process (C), to obtain trisphenols expressed by general formula (1).

Process (C): Eliminate the Xa group of the 4-acylaralkylphenol derivatives expressed by general formula (3) as obtained by process (A), to obtain 4-acylaralkylphenols expressed by general formula (6)

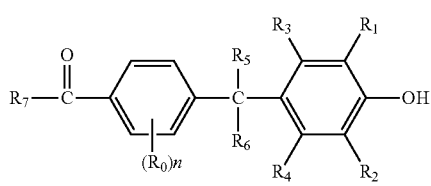

(6)

(in the formula, $R_1$ to $R_4$, $R_5$ and $R_6$, $R_0$ and n, and $R_7$ are the same as the corresponding items in general formula (1)) or, eliminate the Xa group of the trisphenol derivatives expressed by general formula (5) as obtained by process (B), to obtain trisphenols expressed by general formula (1).

A method for producing trisphenols according to an embodiment of the present invention, wherein general formula (2) above is expressed as general formula (2a) where X is an acyl group, or as general formula (2b) where X is a hydrogen atom, and said producing method comprises processes A1, C1 and B1 in this sequence (first producing method) or processes A1, B2 and C2 in this sequence (second producing method), is a favorable embodiment of the present invention.

Process A1: Nucleus-acylate 4-aralkylphenylesters expressed by general formula (2a)

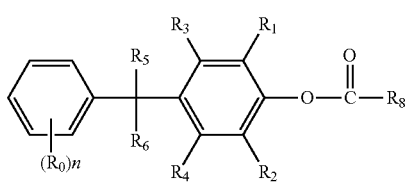

(2a)

(in the formula, $R_1$ to $R_4$, $R_5$ and $R_6$, and $R_0$ and n are the same as the corresponding items in general formula (2), while $R_8$ represents a hydrogen atom or hydrocarbon group, where if n is 1 or greater, $R_0$ is not substituted at the 4-position of the phenyl group)
or, 4-aralkylphenols expressed by general formula (2b)

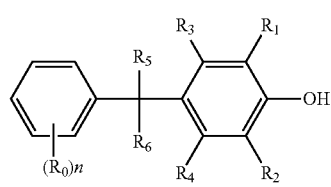

(2b)

(in the formula, $R_1$ to $R_4$, $R_5$ and $R_6$, and $R_0$ and n are the same as the corresponding items in general formula (2), where if n is 1 or greater, $R_0$ is not substituted at the 4-position of the phenyl group)
to obtain 4-acylaralkylphenylesters expressed by general formula (7)

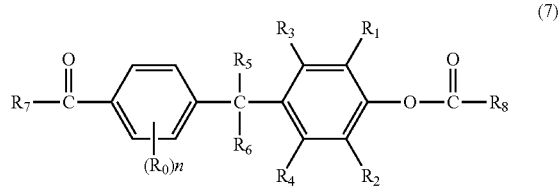

(7)

(in the formula, $R_1$ to $R_4$, $R_5$ and $R_6$, $R_0$, and n and $R_7$ are the same as the corresponding items in general formula (1), while $R_8$ is the same as the corresponding item in general formula (2a)).

Process C1: Hydrolyze, alcoholyze or phenolyze the ester group of the 4-acylaralkylphenylesters expressed by general formula (7), to obtain 4-acylaralkylphenols expressed by general formula (6) above.

Process B1: Next, cause the obtained 4-acylaralkylphenols to undergo condensation reaction with phenols expressed by general formula (4) above, to obtain trisphenols expressed by general formula (1).

Process B2: Cause 4-acylaralkylphenylesters expressed by general formula (7) to undergo condensation reaction with phenols expressed by general formula (4), to obtain monoester-substituted trisphenols expressed by general formula (8)

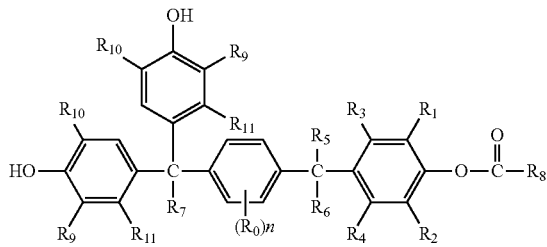

(8)

(in the formula, $R_1$ to $R_4$, $R_5$ and $R_6$, $R_0$ and n, $R_7$, and $R_9$ to $R_{11}$ are the same as the corresponding items in general formula (1), while $R_8$ is the same as the corresponding item in general formula (2a)).

Process C2: Next, hydrolyze, alcoholyze or phenolyze the ester group of the obtained monoester-substituted trisphenols, to obtain trisphenols expressed by general formula (1).

The present invention also provides 4-acylaralkylphenols expressed by formula (6) above, as well as 4-acylaralkylphenylesters expressed by formula (7) above which is a derivative of 4-acylaralkylphenol.

Effects of the Invention

According to the method for producing trisphenols proposed by the present invention, 4-aralkylphenol or derivative thereof used as the starting material is relatively stable against acid and heat and offers excellent storage stability, which is a plus in industrial production, and it can be produced with ease from inexpensive, readily available starting materials such as phenols, styrenes or the like. After this 4-aralkylphenol or derivative thereof is nucleus-acylated, it is caused to undergo condensation reaction with phenols and the leaving group of the 4-acylaralkylphenol derivatives is substituted with a hydrogen atom, to obtain trisphenols of various structures suitable for various purposes. It is also possible to obtain each target product at high purity and high yield by selecting a specified leaving group or reaction method.

In addition, the 4-acylaralkylphenol derivative proposed by the present invention is a new 4-acylaralkylphenol derivative having a bisphenyl molecular skeleton with the acyl group at the para-position in one phenyl ring and the hydroxyl group or acyloxy group at the para-position in the other phenyl ring, and when it is reacted with phenols, trisphenols of various structures suitable for various purposes can be obtained at high purity and high yield. Since this 4-acylaralkylphenol derivative itself has two highly reactive function groups at both ends of the bisphenyl skeletal molecule, it can be used as intermediate reaction products of various types offering excellent heat resistance, etc.

Furthermore, such compound is more stable against acid and heat and offers excellent storage stability compared to conventional material compounds, and can be produced from 4-aralkylphenols which can yet be easily produced from an inexpensive, readily available materials such as phenols or styrenes or the like.

BEST MODE FOR CARRYING OUT THE INVENTION

Under the present invention, the target trisphenols expressed by general formula (1) are produced from the starting material being 4-aralkylphenol derivatives expressed by general formula (2), through a nucleus-acylation process (A)

as well as subsequent phenols condensation process (B) and elimination process (C) for substituting X with a hydrogen atom.

A scheme of a producing method conforming to the present invention is shown below.

methoxy group, ethoxy group, n-propoxy group, isopropoxy group and cyclohexyloxy group, etc. $R_1$ to $R_4$ are preferably a hydrogen atom, alkyl group with 1 to 8 carbon atoms, or alkoxyl group with 1 to 8 carbon atoms, or more preferably are a hydrogen atom or alkyl group with 1 to 4 carbon atoms.

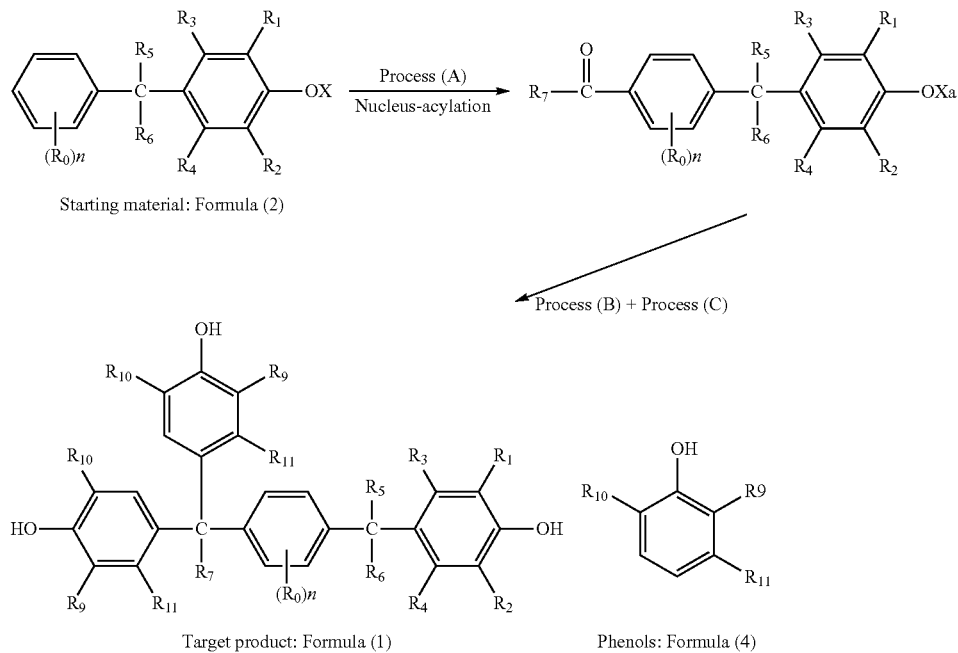

As for the 4-aralkylphenol derivatives expressed by general formula (2), which are used as the materials in the method for producing trisphenols proposed by the present invention, in the formula $R_1$ to $R_4$ each independently represent a hydrogen atom, alkyl group, alkoxyl group, aromatic hydrocarbon group, halogen atom, acyloxy group or hydroxyl group; $R_5$ and $R_6$ each independently represent a hydrogen atom or alkyl group; $R_0$ represents an alkyl group, alkoxyl group or halogen atom; n is 0 or an integer of 1 to 4, where if n is 2 or greater, all $R_0$'s may be the same or different.

Here, if $R_1$ to $R_4$ are an alkyl group, it may be a straight or branched alkyl group with 1 to 10 carbon atoms, or cycloalkyl group with 5 to 10 carbon atoms. Preferably it is a straight or branched alkyl group with 1 to 4 carbon atoms, or cycloalkyl group with 5 or 6 carbon atoms. Specific examples of such alkyl group include the methyl group, ethyl group, n-propyl group, isopropyl group and cyclohexyl group, etc.

The alkyl group may also have a substituent such as a halogen atom, alkoxyl group, hydroxyl group, acyloxy group, phenyl group or the like. Accordingly, specific examples of the alkyl group include the methyl group, ethyl group, isopropyl group, cyclohexyl group, benzyl group, methoxy ethyl group and 3-chloropropyl group, etc.

Also, the alkoxyl group may be, for example, a straight or branched alkoxyl group with 1 to 10 carbon atoms, or cycloalkoxyl group with 5 to 10 carbon atoms. Preferably it is a straight or branched alkoxyl group with 1 to 4 carbon atoms, where if an alkoxyl group with 3 or 4 carbon atoms is used, it may be of straight or branched type. A preferred form of the cycloalkoxyl group is a cycloalkoxyl group with 5 or 6 carbon atoms. Specific examples of such alkoxyl group include the In addition, $R_3$ or $R_4$ preferably are a hydrogen atom, methyl group or ethyl group, and more preferably either $R_3$ or $R_4$ or both is/are hydrogen atom.

The alkyl group of the alkoxyl group may also have a substituent such as a halogen atom, alkoxyl group, hydroxyl group, acyloxy group, phenyl group or the like. Accordingly, specific examples of the alkoxyl group include the methoxy group, ethoxy group and 2-chloroethoxy group, etc.

If an aromatic hydrocarbon group is used, it may be an aromatic hydrocarbon group with 6 to 10 carbon atoms, for example. The aromatic hydrocarbon group may also have a substituent such as an alkyl group, halogen atom, alkoxyl group, hydroxyl group, acyloxy group, phenyl group or the like. Accordingly, specific examples of the aromatic hydrocarbon group include the phenyl group, 1-naphtyl group, 4-methylphenyl group and 4-chlorophenyl group, etc. If the aromatic hydrocarbon group is a phenyl group, preferably the 4-position of the phenyl group has a substituent.

Examples of the halogen atom include bromine, chlorine, fluorine and iodine.

As for the acyloxy group (R—C(O)—O—), the substituent (R) bonded to its carbonyl group may be an aliphatic hydrocarbon group, cyclic hydrocarbon group, aromatic hydrocarbon group or hydrogen atom, but it is preferably an alkyl group or aromatic hydrocarbon group similar to the alkyl group or aromatic hydrocarbon group used when $R_1$ to $R_4$ mentioned above are an alkyl group or aromatic hydrocarbon group, or more preferably is an alkyl group similar to the aforementioned alkyl group.

Accordingly, specific examples of the acyloxy group include the formyloxy group, acetyloxy group, propionyloxy group, benzoyloxy group and toluoyloxy group, etc.

If at least one of $R_1$ to $R_4$ is a hydroxyl group or acyloxy group, preferably both $R_1$ and $R_2$ are not a hydroxyl group or acyloxy group simultaneously, and both $R_1$ and $R_3$ are a hydroxyl group or acyloxy group or either $R_1$ or $R_3$ is a hydroxyl group or acyloxy group, or more preferably either $R_3$ or $R_4$ or both is/are hydrogen atom.

As for the 4-aralkylphenol derivatives expressed by general formula (2) above, in the formula $R_5$ and $R_6$ each independently represent a hydrogen atom or alkyl group, where if an alkyl group is used, it may be a straight or branched alkyl group with 1 to 10 carbon atoms, or cycloalkyl group with 5 to 10 carbon atoms, for example. Preferably it is a straight or branched alkyl group with 1 to 10 carbon atoms, or more preferably an alkyl group with 1 to 4 carbon atoms, where if an alkyl group with 3 or 4 carbon atoms is used, it may be of straight or branched type. Specific examples include the methyl group, ethyl group, n-propyl group, isopropyl group and sec-butyl group etc. Note that while either $R_5$ or $R_6$ may be a hydrogen atom or both may be an alkyl group or hydrogen atom, preferably either $R_5$ or $R_6$ or both is/are a hydrogen atom or primary or secondary alkyl group.

$R_0$ represents an alkyl group, alkoxyl group or halogen atom, where this alkyl group, alkoxyl group or halogen atom is the same as the alkyl group, alkoxyl group or halogen atom used when $R_1$ to $R_4$ mentioned above are an alkyl group, alkoxyl group or halogen atom. The alkyl group is straight or branched, where specific examples of such alkyl group include the methyl group, ethyl group, n-propyl group, isopropyl group and sec-butyl group, etc. If an alkoxyl group is used, it is straight or branched, where specific examples of such alkoxyl group include the methoxy group, ethoxy group, n-propoxy group, isopropoxy group and sec-butoxy group etc.

n is 0 or an integer of 1 to 4, but if n is 2 or greater, all $R_0$'s may be the same or different. Preferably n is 0 or an integer of 1 or 2. $R_0$ preferably is an alkyl group with 1 to 4 carbon atoms.

X represents a hydrogen atom or leaving group that can be substituted with a hydrogen atom (hereinafter also referred to as "Xa"). Here, the leaving group that can be substituted with a hydrogen atom is preferably such that after 4-aralkylphenol derivatives expressed by general formula (2) have been put through the nucleus-acylation process (A), the leaving group (Xa) bonded with the 4-acylaralkylphenol derivatives expressed by general formula (3) or trisphenol derivatives expressed by general formula (5) can be substituted with a hydrogen atom without affecting the 4-acyl group, aralkyl phenol skeleton or trisphenol skeleton. For example, it may be a substituent that can be easily eliminated through hydrolysis, alcoholysis, hydrogenolysis, cleavage reaction, etc., where examples of such leaving group (Xa) include the acyl group, hydrocarbon group and residue obtained by removing the hydroxyl group from sulfonic acid ($R'$—$SO_2$ group; $R'$ represents a hydrocarbon group), etc. To be specific, it may be groups such as the alkylcarbonyl group, alkyl group, alkylsulfonyl group, arylsulfonyl group or the like. Specific examples include the acetyl group, 4-methylphenylcarbonyl group, methyl group, cyclohexyl group, mesyl group, trifluoromethylsulfonyl group, tosyl group and 2-nitrobenzenesulfonyl group, where the acyl group is preferred, and the alkylcarbonyl group such as the acetyl group or the like is more preferred, because it suppresses decomposition of the alkylidene group in the material 4-aralkylphenol derivative expressed by general formula (2) and improves the selectivity of nucleus-acylation reaction.

Accordingly, specific examples of the 4-aralkylphenol derivatives expressed by general formula (2) include p-cumylphenol, 2-methyl-4-cumylphenol, 2,6-dimethyl-4-cumylphenol, 2,3,6-trimethyl-4-cumylphenol, 4-benzylphenol, 4-(1-phenylethyl)phenol, 2-chloro-4-cumylphenol, 2-chloro-4-[(2,5-dimethylphenyl)methyl]-6-methylphenol, 2-phenyl-4-benzylphenol, 1-(4-acetoxyphenyl)-1-methylethylbenzene, 1-tosyloxy-4-(1-phenyl-1-methylethyl)benzene, 1-mesyloxy-4-(1-phenyl-1-methylethyl)benzene and 1-methoxy-4-(1-phenyl-1-methylethyl)benzene, etc.

Such 4-aralkylphenols can be easily obtained through reaction of phenols and styrenes or 1-hydroxy alkylbenzenes according to the methods described in U.S. Pat. No. 2,247, 402, U.S. Pat. No. 2,714,120 and U.S. Pat. No. 2,769,844, etc.

If X is an acyl group, such 4-aralkylphenylesters can be easily obtained by any known method of acylation, such as one where the phenolic hydroxyl group of the 4-aralkylphenol is acylated using acylation agent such as acetic anhydride, propionyl chloride or the like.

If X is a hydrocarbon group, such hydrocarbon group may be similar to one used when $R_1$ to $R_4$ mentioned above are an aromatic hydrocarbon group or alkyl group. If X is an alkyl group, it may be a straight, branched or cyclic alkyl group with around 1 to 10 carbon atoms, where lower alkyl group such as the methyl group, ethyl group, propyl group or the like is preferable. Such 4-aralkylphenyl ethers can be easily obtained by any known method, such as one where a 4-aralkylphenol is reacted with a halogenated alkyl in the presence of a base (reaction formula: Example 1). It can also be obtained by reacting alkoxylbenzenes and styrenes in the presence of catalyst such as lithium iodine, bismuth trichloride or the like (reaction formula: Example 2) as described in Tetrahedoron Letters 48 (2007) 6881-6885 and Euro. J. Org. Chem. 2006, 4231-4236.

Reaction Formula

Example 1

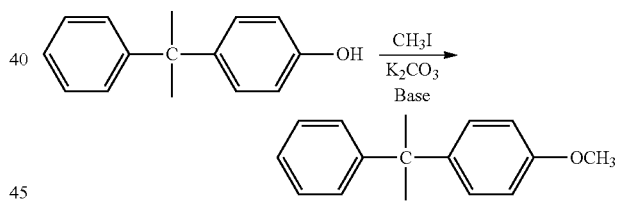

Reaction Formula

Example 2

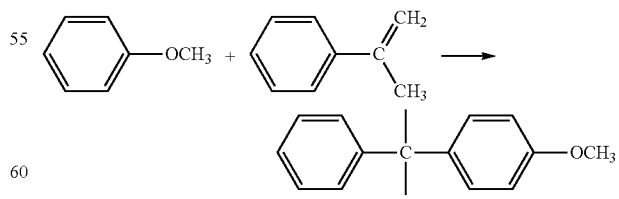

If X is a residue obtained by removing the hydroxyl group from sulfonic acid ($R'$—$SO_2$ group; $R'$ represents a hydrocarbon group), in general formula (2), the hydrocarbon group $R'$ is similar to one used when $R_1$ to $R_4$ mentioned above are an aromatic hydrocarbon group or alkyl group, and such 4-aralkylphenol derivative whose X is a residue obtained by removing the hydroxyl group from sulfonic acid can be easily obtained by any known method such as one where 4-aralkylphenols expressed by general formula (2b) are reacted with halogenated sulfonyl hydrocarbon such as tosyl chloride, mesyl chloride or the like in the presence of organic amine such as pyridine or the like or inorganic base such as potassium carbonate or the like.

In the meantime, with respect to the target product of the present invention, or specifically trisphenols expressed by general formula (1) above, in the formula $R_1$ to $R_4$, $R_5$ and $R_6$, $R_0$ and n are the same as the corresponding items in general formula (2).

$R_7$ represents a hydrogen atom or alkyl group, where if an alkyl group is used, it is the same as the alkyl group used when $R_1$ to $R_4$ mentioned above are an alkyl group, and it is preferably of primary or secondary type. Accordingly, specific examples of such alkyl group include the methyl group, ethyl group, isopropyl group, cyclohexyl group, benzyl group, methoxyethyl group and 3-chloropropyl group, etc. Also, the alkyl group preferably has 1 to 4 carbon atoms.

Also, $R_9$ to $R_{11}$ each independently represent a hydrogen atom, alkyl group, alkoxyl group, aromatic hydrocarbon group, halogen atom or hydroxyl group, where the alkyl group, alkoxyl group, aromatic hydrocarbon group or halogen atom is the same as the alkyl group, alkoxyl group, aromatic hydrocarbon group or halogen atom used when $R_1$ to $R_4$ mentioned above are an alkyl group, alkoxyl group, aromatic hydrocarbon group or halogen atom, and a hydrogen atom, alkyl group with 1 to 4 carbon atoms, cycloalkyl group with 5 or 6 carbon atoms, alkoxyl group with 1 to 4 carbon atoms, or phenyl group is preferred. It is also preferable from the production viewpoint that both $R_9$ and $R_{10}$ should not be a hydroxyl group simultaneously, and if $R_7$ is an alkyl group, preferably $R_{11}$ is a hydrogen atom from the production viewpoint.

Accordingly, specific examples of the trisphenols expressed by general formula (1) include the following, and the like:

1-[α-methyl-α-(3-methyl-4-hydroxyphenyl)ethyl]-4-[α,α-bis(3-methyl-4-hydroxyphenyl)ethyl]benzene;

1-[α-methyl-α-(3-methoxy-4-hydroxyphenyl)ethyl]-4-[α,α-bis(3-methoxy-4-hydroxyphenyl)ethyl]benzene;

1-[α-methyl-α-(4-hydroxyphenyl)ethyl]-4-[α,α-bis(4-hydroxyphenyl)ethyl]benzene; and 1-[α-methyl-α-(3-cyclohexyl-4-hydroxyphenyl)ethyl]-4-[α,α-bis(3-cyclohexyl-4-hydroxyphenyl)ethyl]benzene.

Also regarding the 4-aralkylphenylesters expressed by general formula (2a), which are one of the 4-aralkylphenol derivatives expressed by general formula (2) and used as the material in the method for producing trisphenols proposed by the present invention, in the formula $R_1$ to $R_4$, $R_5$ and $R_6$, $R_0$ and n are the same as the corresponding items in general formula (2). $R_8$ is a hydrogen atom or hydrocarbon group, and if a hydrocarbon group is used, it may be an unsaturated aliphatic hydrocarbon group, alkyl group or aromatic hydrocarbon group, etc. If an alkyl group or aromatic hydrocarbon group is used, it is the same as the alkyl group or aromatic hydrocarbon group used when $R_1$ to $R_4$ are an alkyl group or aromatic hydrocarbon group in general formula (2). An alkyl group is preferable, and as the species, an alkyl group of primary or secondary type is preferable.

As for the 4-aralkylphenyl ethers expressed by general formula (2c), which are a one of 4-aralkylphenol derivatives expressed by general formula (2) and used as the material in the method for producing trisphenols proposed by the present invention, in the formula $R_1$ to $R_4$, $R_5$ and $R_6$, $R_0$ and n are the same as the corresponding items in general formula (2), where R represents a hydrocarbon group. The hydrocarbon group constituting R may be an unsaturated aliphatic hydrocarbon group, alkyl group or aromatic hydrocarbon group, etc. If an alkyl group or aromatic hydrocarbon group is used, it is the same as the alkyl group or aromatic hydrocarbon group used when $R_1$ to $R_4$ are an alkyl group or aromatic hydrocarbon group in general formula (2). An alkyl group is preferable, and as the species, an alkyl group of primary or secondary type is preferable.

Under the method for producing trisphenols proposed by the present invention, it is preferable to use reaction scheme 1 as shown below for production if X in the 4-aralkylphenol derivative being the material expressed by general formula (2) is an acyl group according to general formula (2a) or is a hydrogen atom according to general formula (2b):

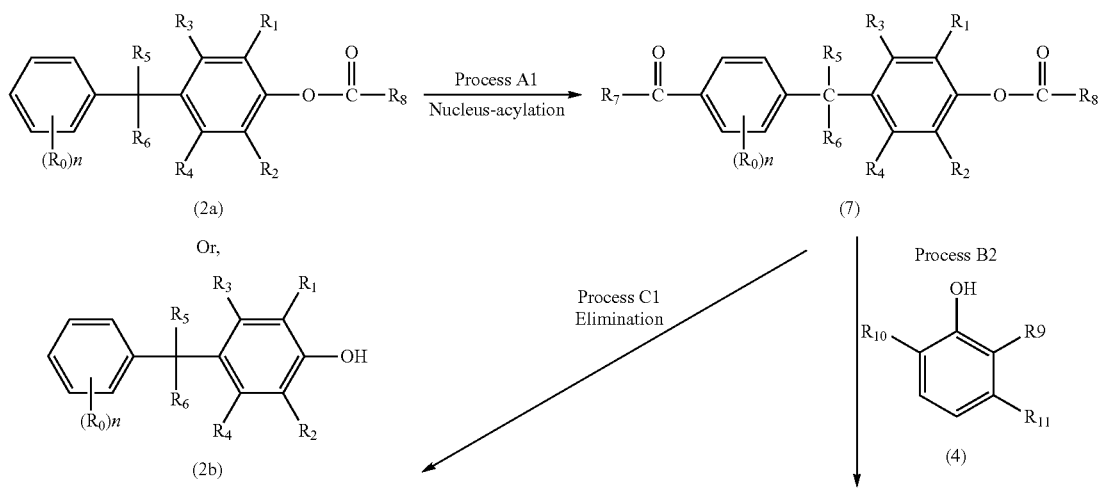

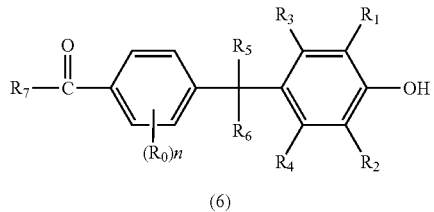

(6)

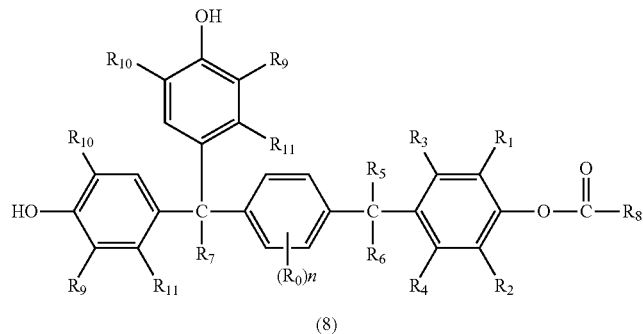

(8)

Process B1

(4)

Process C2
Elimination

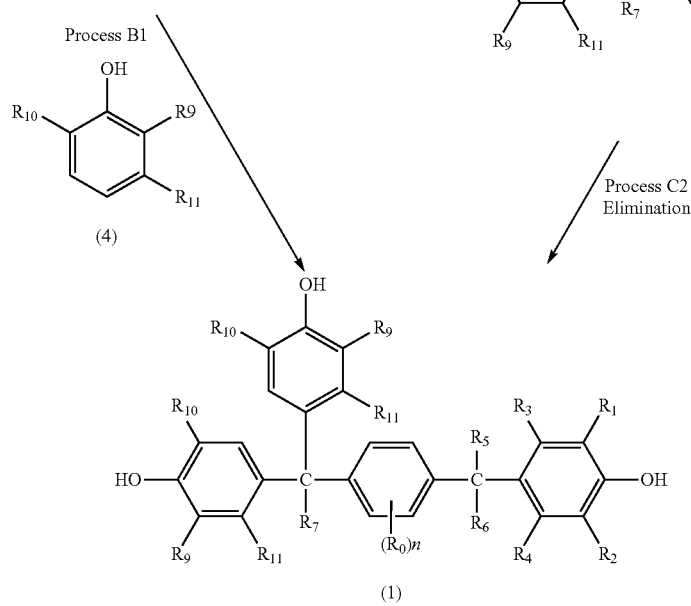

(1)

Next, processes A1 and A under the producing method proposed by the present invention are explained.

Under the producing method proposed by the present invention, 4-aralkylphenol derivatives expressed by general formula (2) above, or preferably 4-aralkylphenylesters expressed by general formula (2a) or 4-aralkylphenols expressed by general formula (2b) above, are used as the starting materials. Then, as illustrated by the producing scheme, the starting materials are nucleus-acylated in process A1 using acylation agent such as acetylchloride, acetic anhydride or the like if the starting materials are 4-aralkylphenylesters expressed by general formula (2a), after which an acyl group is introduced to the 4-position of the phenyl group in the aralkyl group to obtain 4-acylaralkylphenylesters expressed by general formula (7). The starting materials, or 4-aralkylphenylesters expressed by general formula (2a), can be obtained by, for example, acylating the hydroxyl group of 4-aralkylphenols expressed by general formula (2b) that corresponds to general formula (2) where X is a hydrogen atom.

If the starting materials are 4-aralkylphenols expressed by general formula (2b), 4-acylaralkylphenylesters expressed by general formula (7) can also be obtained via acylation of the hydroxy group and nucleus-acylation of the phenyl group using the same reaction process in process A1. In this case, the hydroxyl group is acylated first, and then the phenyl group is nucleus-acylated. Also when the starting materials are 4-aralkylphenol derivatives expressed by general formula (2) where X is a leaving group other than the acyl group, 4-acylaralkylphenol derivatives expressed by general formula (3), whose leaving group Xa corresponds to that of the material 4-aralkylphenol derivatives, can be obtained via nucleus-acylation in the same manner as when the 4-aralkylphenylester expressed by general formula (2a) is used.

Any known acylation reaction can be used for the nucleus-acylation reaction, or acylation reaction of the hydroxy group. Any acylation agent can be used as long as it is being used as such, but it preferably is halogenated acyl expressed by general formula (11) below or carboxylic acid anhydride expressed by general formula (12) below, etc.:

General Formula (11)

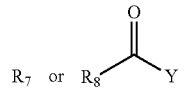

General Formula (12)

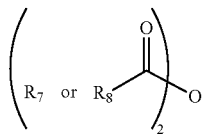

(in the formula, $R_7$ represents a hydrogen atom or alkyl group, $R_8$ represents a hydrogen atom or hydrocarbon group, Y represents a halogen atom, and $R_7$ or $R_8$ corresponds to $R_7$ or $R_8$ in general formula (7), respectively).

The alkyl group constituting $R_7$ is the same as the alkyl group used when $R_1$ to $R_4$ are an alkyl group in general formula (2), while the hydrocarbon group constituting $R_8$ may be an unsaturated aliphatic hydrocarbon group, alkyl group or aromatic hydrocarbon group, etc., where the alkyl group or aromatic hydrocarbon group is the same as the alkyl group or aromatic hydrocarbon group used when $R_1$ to $R_4$ are an alkyl group or aromatic hydrocarbon group in general formula (2).

Accordingly, specific examples of the acylation agent suitable for general formula (11) or general formula (12) having the substituent $R_7$ include formylchloride, acetylchloride, acetylbromide, propionyl chloride, acetic anhydride, monochloroacetic acid anhydride and propionic anhydride, etc., while specific examples of the acylation agent suitable for general formula (11) or general formula (12) having the substituent $R_8$ include formylchloride, acetylchloride, acetylbromide, propionyl chloride, benzoyl chloride, toluic acid chloride, acetic anhydride, monochloroacetic acid anhydride, propionic anhydride, succinic anhydride and maleic anhydride, etc.

Acylation in process A1 of the 4-aralkylphenols expressed by general formula (2b) above may be such that the hydroxyl group and phenyl ring of the 4-aralkylphenol are acylated simultaneously (process A1b below: one-stage method), or the hydroxyl group is protected with acyl group such as an acetyl group or the like first, followed by nucleus-acylation of the phenyl ring (process A1a below: two-stage method). The former one-stage acylation method is preferable. The nucleus-acylation reaction in process A1a below is the same as nucleus-acylation reaction in process A1 when the starting material above is 4-aralkylphenylesters expressed by general formula (2a).

[Process A1b: Reaction Scheme for One-Stage Acylation]

Under this method, the hydroxyl group and phenyl nucleus are acylated in one stage, which means $R_7=R_8$ and for the acylation agent, one suitable for general formula (11) or general formula (12) having the substituent $R_7$ is used, for example.

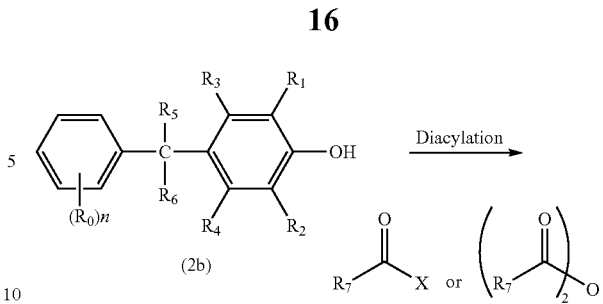

[Process A1a: Reaction Scheme for Two-Stage Acylation]

Under this method, acylation is implemented in two stages, which means $R_7$ and $R_8$ may be the same or different and for the acylation agent, one suitable for general formula (11) having the substituent $R_8$, general formula (11) having acylation agent suitable for general formula (12) and the substituent $R_7$, and general formula (12) are used in sequence.

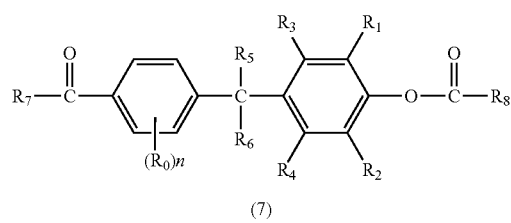

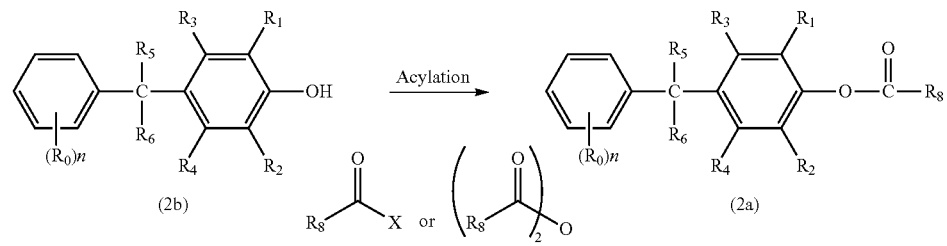

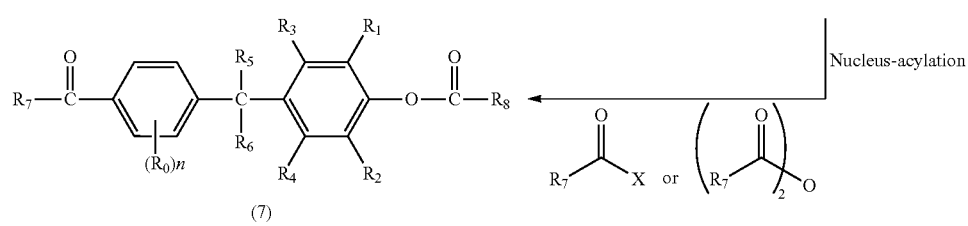

Accordingly, in the 4-acylaralkylphenol derivative expressed by general formula (3) and in $R_7$ in the formula and 4-acylaralkylphenylesters expressed by general formula (7), the substituent $R_7$ or $R_8$ in the formula is derived from $R_7$ or $R_8$ being a halogenated acyl which is the acylation agent used in the acylation process expressed by general formula (11) above, or carboxylic acid anhydride expressed by general formula (12) above. Under the one-stage acylation method where the hydroxyl group and phenyl group are acylated at the same time in process A1, $R_7$ and $R_8$ are the same. Under the two-stage acylation process where the hydroxyl group is acylated first and then the phenyl nucleus is acylated, $R_7$ and $R_8$ may be the same or different.

Normally an acylation catalyst is used in acylation reaction. Any acylation catalyst can be used as long as it is an acid catalyst capable of acylating carbon atoms in aromatic rings such as the benzene ring or the like, but examples include Lewis acid, solid acid and protonic acid, etc.

Examples of Lewis acid include metal halogenides such as aluminum chloride, tin chloride (IV), copper chloride, (anhydrous) ferric chloride (III) or the like, but aluminum chloride is preferred. Examples of solid acid include heteropolyacids such as zeolite, phosphotungstic acid, phosphomolybdic acid, silicotungstic acid, silicomolybdic acid or the like, and metal salts of heteropolyacids, etc. Examples of protonic acid include hydrogen chloride gas, sulfuric acid and polyphosphoric acid, etc. Of the above, Lewis acid is preferred.

The molar ratio of acylation agent to 4-aralkylphenol derivatives expressed by general formula (2) (acylation agent/ 4-aralkylphenol derivatives) preferably is in a range of [{1+(number of hydroxyl groups in 4-aralkylphenol derivatives molecule)}]/1 to [1.25×{1+(number of hydroxyl groups in 4-aralkylphenol derivatives molecule)}]/1. For example, in the case of 4-aralkylphenols expressed by general formula (2b) where X is a hydrogen atom and there is no other hydroxyl group, the diacylation method where the hydroxyl group and phenyl nucleus are acylated in the same reaction process (one-stage acylation method) preferably uses a range of 2/1 to 2.5/1, or more preferably a range of 2.1/1 to 2.3/1. On the other hand when acylating only the phenyl nucleus of 4-aralkylphenol derivatives where X is not a hydrogen atom and there is no hydroxyl group, the range preferably is 1/1 to 1.25/1, or more preferably 1.1/1 to 1.2/1. The aforementioned hydroxyl group preferably is a phenolic hydroxyl group.

If Lewis acid is used, the molar ratio of Lewis acid to carbonyl groups in acylation agent (number of moles in Lewis acid/[number of moles in acylation agent x number of carbonyl groups in acylation agent molecule]) preferably is in a range of 1/1 to 1/1.1, or more preferably is 1/1. If the molar ratio is too high, the yield drops. Too low a molar ratio is not desirable, either, because the reaction ratio of acylation agent drops.

Specifically, the molar ratio of Lewis acid to acylation agent (Lewis acid/acylation agent) preferably is in a range of 1/1 to 1/1.1, or more preferably is 1/1, in the case of halogenated acyl. If an acid anhydride is used, the molar ratio preferably is in a range of 2/1 to 2/1.1, or more preferably is 2/1. If the 4-aralkylphenol derivatives expressed by general formula (2) have oxo (=O) such as an acyloxy group, alkyl sulfonyloxy group or the like then the molar volume of Lewis acid used preferably is in a range of (number of moles in acylation agent x number of carbonyl groups in acylation agent molecule) to ([number of moles in acylation agent x number of carbonyl groups in acylation agent molecule]+[number of moles in 4-aralkylphenol derivatives x number of oxo groups in 4-aralkylphenol derivatives molecule]). Therefore, when acylating 4-aralkylphenol derivatives where X is an acyloxy group and there is no oxo group or hydroxyl group, for example, the molar ratio (Lewis acid/acylation agent) preferably is in a range of 1/1 to 2/1 if the acylation agent is a halogenated acyl. In the case of an acid anhydride, the molar ratio (Lewis acid/acylation agent) preferably is in a range of 1/1 to 3/1.

Depending on the activity of the catalyst used, an excessively high reaction temperature makes it easy to cause a side reaction, such as the $R_5$ and $R_6$ substituted alkylidene group being severed, etc., thereby resulting in low yield. Accordingly, the reaction temperature preferably is in a range of −50 to 50° C., or −20 to 20° C. when Lewis acid is used, or more preferably is in a range of 0 to 10° C.

For this reaction, a reaction solvent generally used for Friedel-Crafts reaction is normally used. Solvents that can be used include halogenated saturated hydrocarbons such as chloroform, methylenechloride or the like, as well as chlorobenzene and carbon disulfide.

Under these reaction conditions, the reaction normally completes in several hours up to less than ten plus several hours. If Lewis acid is used, the reaction process normally takes the form of mixing Lewis acid and acylation agent to form a complex (or adduct) and then dripping a solution of 4-aralkylphenol derivatives into a solution of this complex.

If the acylation agent is formylhalogen, the compound itself is unstable and thus carbon monoxide and hydrogen chloride can also be used to implement the above acylation reaction in the presence of aluminum chloride or copper chloride.

In the case of two-stage acylation where the hydroxyl group of the 4-aralkylphenol is protected by acyl group such as an acetyl group or the like and then the phenyl ring is nucleus-acylated, the hydroxyl group is acylated first, after which the same acylation reaction is repeated using the same acylation agent or a different acylation agent. In this case, use of an excessive amount of carboxylic acid anhydride in the first reaction, or acylation of the hydroxyl group, is preferred because this normally eliminates the need for Lewis acid and makes the reaction easy.

Also, any known refining method can be used to refine the target product from the liquid reaction mixture, as necessary. If the catalyst is Lewis acid, for example, acid aqueous solution such as aqueous solution of hydrochloric acid or the like is added to decompose the adduct of the acid and product to deactivate the acid and dissolve it in the water layer. If necessary, a solvent that separates from water is added to separate and remove the water layer to obtain the oil layer. The obtained oil layer is washed in water and the solvent and material (phenols, if multi-nuclear) are distilled out from the obtained oil layer as necessary, after which a solvent is added to cause crystallization or precipitation to obtain crystalline or non-crystalline solids. If necessary, such as when the purity of crystal or solids is low, etc., recrystallization or reprecipitation may be repeated once or multiple times. This way, highly pure 4-acylaralkylphenylesters can be achieved in process A1.

Specific examples of such 4-acylaralkylphenylesters include the following or the like:
1-acetyl-4-{1-methyl-1-(4-acetyloxyphenyl)ethyl}benzene;

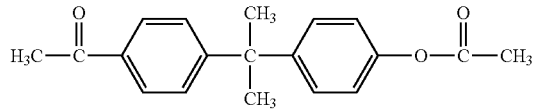

1-acetyl-4-{1-methyl-1-(3-methyl-4-acetyloxyphenyl)ethyl}benzene;
1-acetyl-4-{1-methyl-1-(3,5-dimethyl-4-acetyloxyphenyl)ethyl}benzene;
1-acetyl-4-{1-methyl-1-(2,3,5-trimethyl-4-acetyloxyphenyl)ethyl}benzene;
1-acetyl-4-{1-methyl-1-(3-cyclohexyl-4-acetyloxyphenyl)ethyl}benzene;
1-acetyl-4-{1-methyl-1-(3-isobutyl-4-acetyloxyphenyl)ethyl}benzene;
1-butyryl-4-{1-methyl-1-(4-butyryloxyphenyl)ethyl}benzene;
1-acetyl-4-{(4-acetyloxyphenyl)methyl}benzene;
1-acetyl-4-{1-(4-acetyloxyphenyl)ethyl}benzene; and
1-propionyl-4-{(4-acetyloxyphenyl)methyl}benzene.

Next, processes C1 and B1 in the producing method proposed by the present invention are explained.

Process C1 is a reaction process to obtain 4-acylaralkylphenols expressed by general formula (6) by hydrolyzing, alcoholyzing and/or phenolyzing the ester group of the 4-acylaralkylphenylesters expressed by general formula (7) as obtained in process A1 above, according to the aforementioned reaction scheme, while process B1 is a reaction process to obtain the target product, or trisphenols expressed by general formula (1), by subsequently causing the obtained 4-acylaralkylphenols to undergo condensation reaction with a phenol expressed by general formula (4).

In process C1, any known method can be used for hydrolysis, alcoholysis or phenolysis of the ester group. In the case of decomposition using water, alcohols and/or phenols, for example, there is no limitation regarding the molar ratio of water, alcohols and/or phenols to 4-acylaralkylphenylesters ([water, alcohols and/or phenols]/4-acylaralkylphenylesters), but it should normally be in a range of 1/1 to 100/1, or preferably is in a range of 10/1 to 30/1, because if the molar ratio is too high, the volume efficiency drops. Also for alcohol, aliphatic alcohol such as methanol, ethanol or the like is preferred. For phenol, mononuclear phenol such as phenol, o-cresol or the like is preferred.

The decomposition reaction is normally implemented in the presence of an alkali or acid catalyst, but use of alkali is preferred from the viewpoints of reaction speed and yield. Examples of alkali include alkali metal hydroxides such as sodium hydroxide, potassium hydroxide or the like, as well as organic strong bases such as tetramethyl ammonium hydroxide, or the like. The molar ratio of alkali to 4-acylaralkylphenylesters (alkali/number of ester groups in 4-acylaralkylphenylesters molecule) should normally be in a range of 1/1 to 5/1, or preferably is in a range of 2/1 to 3/1.

The reaction temperature should normally be in a range of 0 to 150° C., or preferably is in a range of 50 to 100° C. If the material 4-acylaralkylphenylesters has a high melting point and agitation is difficult at the time of reaction, a solvent can be used. Any solvent can be used as long as it does not inhibit the reaction or cause any side reaction, but examples include aliphatic ketones such as methyl isobutyl ketone or the like, lower aliphatic alcohols such as methanol, isopropanol or the like, aromatic hydrocarbons such as toluene or the like, and ethers such as tetrahydrofuran or the like. If water alone is used to implement hydrolysis, preferably a small amount of water-soluble alcohol such as methanol is added to water because otherwise the reaction speed is too slow.

After the reaction, any known refining method can be used to refine the target product from the liquid reaction mixture, as necessary. For example, an aqueous solution of acid is added to the obtained liquid reaction mixture to neutralize the alkali, and if necessary a solvent that separates from water is added to separate and remove the water layer and obtain the oil layer containing the target product. The obtained oil layer is washed with water and, after distilling out the solvent, etc., from the obtained oil layer as necessary, a solvent is added again to cause crystallization or precipitation to obtain crystalline or non-crystalline solids. If necessary, such as when the purity of crystal or solids is low etc., recrystallization or reprecipitation may be repeated once or multiple times. This way, highly pure 4-acylaralkylphenols expressed by general formula (6) can be achieved.

Specific examples of such 4-acylaralkylphenols include following, or the like:
1-acetyl-4-{1-methyl-1-(4-hydroxyphenyl)ethyl}benzene;
1-acetyl-4-{1-methyl-1-(3-methyl-4-hydroxyphenyl)ethyl}benzene;

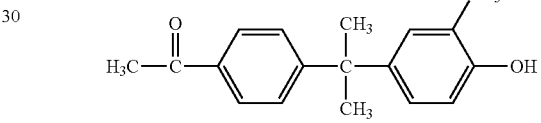

1-acetyl-4-{1-methyl-1-(3,5-dimethyl-4-hydroxyphenyl)ethyl}benzene;
1-acetyl-4-{1-methyl-1-(2,3,5-trimethyl-4-hydroxyphenyl)ethyl}benzene;
1-acetyl-4-{1-methyl-1-(3-cyclohexyl-4-hydroxyphenyl)ethyl}benzene;
1-acetyl-4-{1-methyl-1-(3-isobutyl-4-hydroxyphenyl)ethyl}benzene;
1-butyryl-4-{1-methyl-1-(4-hydroxyphenyl)ethyl}benzene;
1-acetyl-4-{(4-hydroxyphenyl)methyl}benzene; and
1-acetyl-4-{1-(4-hydroxyphenyl)ethyl}benzene.

Next in process B1, the 4-acylaralkylphenols obtained above are caused to undergo condensation reaction with phenols expressed by general formula (4) to obtain trisphenols. Any known reaction method can be used for the condensation reaction. Here, specific examples of the phenols expressed by general formula (4) include phenol, o-cresol, 2-ethylphenol, catechol, 2-cyclohexylphenol, 2-methoxyphenol, 2-isopropylphenol, 2-chlorophenol, 2-bromophenol, 2-phenylphenol, 2-benzylphenol and 2,6-xylenol, etc.

At the time of reaction, the molar ratio of phenols to 4-acylaralkylphenols (phenols/4-acylaralkylphenols) should normally be in a range of 2/1 to 10/1, or preferably is in a range of 3/1 to 5/1. The catalyst used for the reaction preferably is an inorganic acid or organic acid of high to medium strength. Examples of inorganic acid include 35% hydrochloric acid, hydrogen chloride gas, sulfuric acid and phosphoric acid, etc. Preferred forms of organic acid are organic sulfonic acid and carboxylic acid, where examples include p-toluene sulfonic acid, methane sulfonic acid and oxalic acid, etc. Of these, a strong acid, especially hydrochloric acid gas or concentrated hydrochloric acid is preferred. The amount of catalyst used varies depending on the type of catalyst, but normally it should be in range of 1 to 50 percent by weight relative to phenols. Also, use of an appropriate amount of co-catalyst with the main catalyst is preferable because it improves the yield, especially when $R_7$ in general formula (6) is an alkyl group.

For the co-catalyst, a compound or polymer compound containing a mercapto group is preferred, where specific examples include alkyl mercaptans such as n-dodecylmercaptan, methylmercaptan or the like, mercaptan carboxylic acids such as mercaptoacetic acid, β-mercaptopropionic acid or the like, and cation exchange resins or organic polymer siloxane containing a mercapto group, etc.

A solvent may or may not be used for the reaction, but if the molar ratio of phenols/4-acylaralkylphenols is low or the phenols have a high melting point and making it into solution is difficult, a solvent may be used. Examples of such solvent include lower aliphatic alcohols such as methanol, butanol or the like, aromatic hydrocarbons such as toluene, xylene or the like, and aliphatic ketones such as methyl isobutyl ketone or the like, and if the material used has a high melting point and easily soluble in water such as catechol, water may be used as the reaction solvent. Lower aliphatic alcohol is preferred.

The amount of solvent used is not specifically limited, but it should normally be in a range of 0.1 time by weight to 10 times by weight, or preferably is in a range of 0.5 time by weight to 2 times by weight, relative to the phenols used.

The reaction temperature should normally be in a range of 0 to 100° C., or preferably is in a range of 30 to 60° C.

The reaction is implemented by dripping a solvent solution of 4-acylaralkylphenols into a solvent solution of phenols and catalyst in an ambience of nitrogen gas at 40° C., for example.

After the reaction, any known refining method can be used to refine the target product from the liquid reaction mixture, as necessary. For example, alkali water such as aqueous sodium hydroxide or the like is added to the obtained liquid reaction mixture to neutralize the acid, and if necessary, solvent that can be separated from water such as toluene, xylene, methyl isobutyl ketone, ether or the like is added to separate and remove the water layer, after which the water layer is separated and removed to obtain the oil layer containing the target product. The obtained oil layer is washed with water and, after distilling out the solvent, etc., from the obtained oil layer as necessary, a solvent is added again to cause crystallization or precipitation to obtain crystalline or non-crystalline solids. If necessary, such as when the purity of crystal or solids is low, etc., recrystallization or reprecipitation may be repeated once or multiple times. By implementing processes A1, C1 and B1 in this sequence (first producing method), the target product of the producing method proposed by the present invention, or highly pure trisphenol, can be obtained.

Next, processes B2 and C2 in the producing method proposed by the present invention are explained.

Process B2 is a reaction process to obtain monoester-substituted trisphenol expressed by general formula (8) by causing 4-acylaralkylphenylesters expressed by general formula (7) as obtained by process A1 above to undergo condensation reaction with phenols expressed by general formula (4) according to the above reaction scheme, while process C2 is a reaction process to obtain the target product, or trisphenols expressed by general formula (1), by subsequently hydrolyzing, alcoholyzing and/or phenolyzing the ester group of the obtained monoester-substituted trisphenol.

Here, the phenols expressed by general formula (4) is the same as the phenols mentioned in connection with process B1 above. Also in the condensation reaction of 4-acylaralkylphenylesters and phenols, the acyl group bonded to the 4-position of the phenyl group is reacted, which means that, just like in the condensation reaction mentioned in connection with process B1 above, similar conditions can be used for the molar ratio of phenols and material compound (4-acylaralkylphenylesters), catalyst and its amount, use of co-catalyst, solvent and its amount, reaction temperature, reaction method, etc. In this reaction in process B2, the ester group of the 4-acylaralkylphenylesters expressed by general formula (7) may be partially hydrolyzed or shift to the hydroxyl group of the reaction product, etc., but it will not affect the reaction yield at all because the ester group is hydrolyzed next.

After the reaction, any known refining method can be used to refine the target product from the liquid reaction mixture, as necessary. For example, a method similar to the one mentioned in connection with process B1 above can be used to obtain monoester-substituted trisphenols expressed by general formula (8).

Next in process C2, the ester group of the monoester-substituted trisphenols obtained above is hydrolyzed, alcoholyzed and/or phenolyzed.

Any known method can be used for hydrolysis, alcoholysis and/or phenolysis of the ester group of the monoester-substituted trisphenols. In the case of decomposition using water, alcohol and/or phenol, for example, conditions similar to those for hydrolysis, alcoholysis and/or phenolysis as mentioned in connection with process C1 above can be used for the molar ratio of water, alcohols and/or phenols and material compound (monoester-substituted trisphenols), alkali and its amount, use of solvent and its amount, reaction temperature, reaction method, etc. If an acid catalyst is used, it may be hydrochloric acid, hydrogen chloride gas, sulfuric acid, p-toluenesulfonic acid or methanesulfonic acid, etc., while the amount of acid catalyst used should normally be in a range of 0.1 to 10 mol, or preferably is in a range of 1 to 5 mol, per mol of the ester group in the material compound. After the reaction, any known refining method can be used to refine the target product from the liquid reaction mixture, as necessary. For example, a method similar to the one mentioned in connection with process C1 above can be used. By implementing processes A1, B2 and C2 in this sequence (second producing method), the target product of the present invention, or trisphenols expressed by general formula (1), can be obtained. When the 4-acylaralkylphenylester expressed by general formula (7) as obtained by process A1 is reacted in the subsequent process, if reaction conditions for condensation reaction (process B1 or B2) and compounds used are common to reaction conditions and compounds used for hydrolysis, alcoholysis or phenolysis (process C1 or C2), the condensation reaction and hydrolysis, alcoholysis or phenolysis can be implemented in the same process. Even if the conditions are such that either reaction is incomplete, the reaction product may be isolated and the incomplete reaction can be continued, or the reaction product may be refined to obtain the target trisphenol.

Also when the material 4-aralkylphenol derivative expressed by general formula (2) is 4-aralkylphenylethers expressed by general formula (2c) whose X is a hydrocarbon group, a method for producing trisphenols can be presented that comprises either the producing method where processes A2, C3 and B1 mentioned above are implemented in this sequence (third producing method), or producing method where processes A2, B3 and C4 are implemented in this sequence (fourth producing method).

Process A2: Nucleus-acylate 4-aralkylphenylethers expressed by general formula (2c)

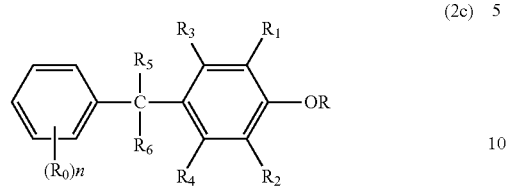

(2c)

(in the formula, $R_1$ to $R_4$, $R_5$ and $R_6$, $R_0$ and n are the same as the corresponding items in general formula (2), while R represents a hydrocarbon group, where if n is 1 or greater, $R_0$ is not substituted at the 4-position of the phenyl group) to obtain 4-acylaralkylphenylethers expressed by general formula (9)

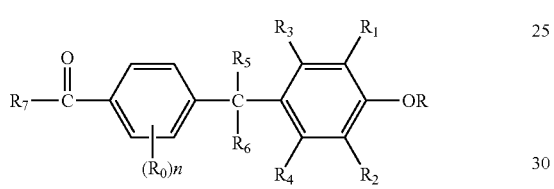

(9)

(in the formula, $R_1$ to $R_4$, $R_5$ and $R_6$, $R_0$ and n, and $R_7$ are the same as the corresponding items in general formula (1), while R is the same as R in general formula (2c)).

Process C3: Cleave the ether group of the 4-acylaralkylphenylethers expressed by general formula (9) as obtained by process A2 to obtain 4-acylaralkylphenol expressed by general formula (6) above.

Process B3: Cause the 4-acylaralkylphenylethers obtained by process A2 to undergo condensation reaction with phenols expressed by general formula (4) above, to obtain monoether substituted trisphenol expressed by general formula (10)

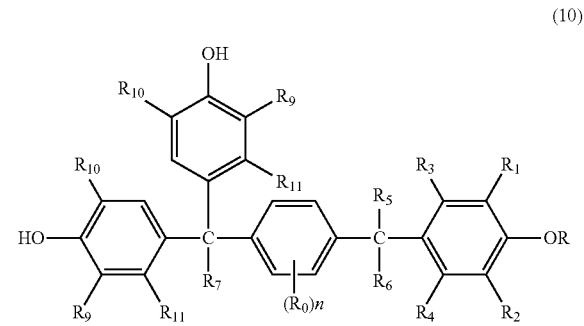

(10)

(in the formula, $R_1$ to $R_4$, $R_5$ and $R_6$, $R_0$ and n, $R_7$, and $R_9$ to $R_{11}$ are the same as the corresponding items in general formula (1), while R is the same as the corresponding item in general formula (2c)).

Process C4: Cleave the ether group of the monoether substituted trisphenol expressed by general formula (10) as obtained by process B3 to obtain trisphenols expressed by general formula (1).

Reaction Scheme 2

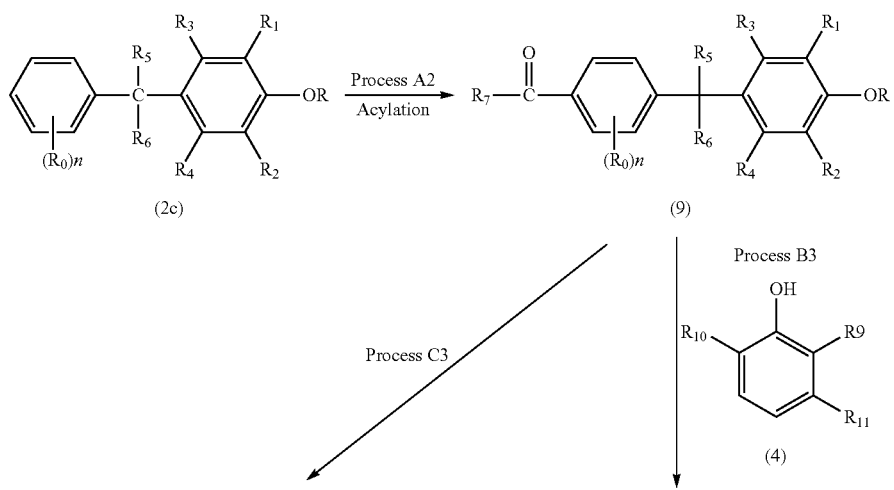

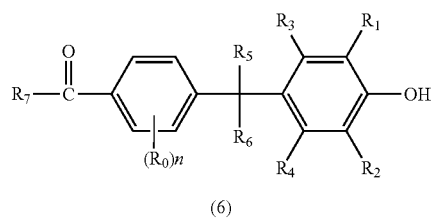

(6)

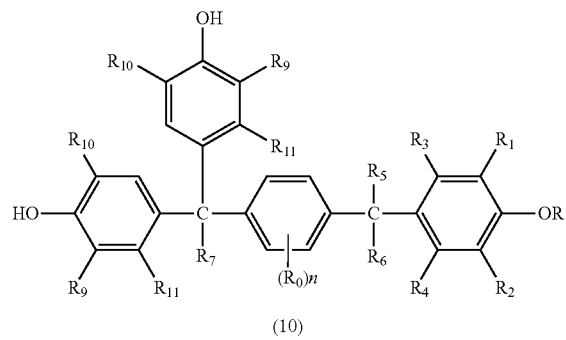

(10)

Process B1

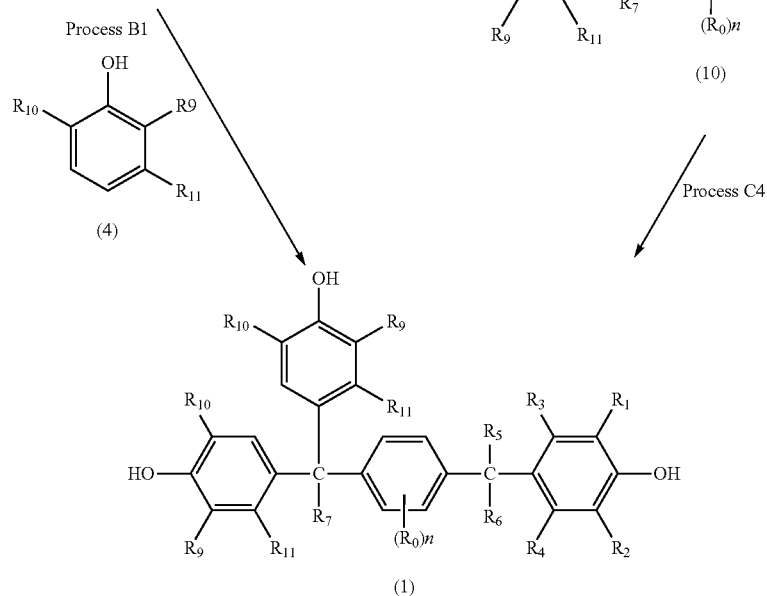

(4)

(1)

Process C4

Here, the nucleus-acylation reaction in process A2 is such that acylation is implemented using acylation agent such as acetylchloride, acetic anhydride or the like to introduce an acyl group to the 4-position of the phenyl nucleus of the aralkyl group, in order to obtain 4-acylaralkylphenylethers expressed by general formula (9). Any known acylation reaction can be used. For example, it may be similar to the nucleus-acylation reaction in the second stage of the two-stage acylation reaction method (process A1a) described in connection with process A1 above.

Also in process C3, any known cleavage reaction relating to phenylether can be used. For example, implementing cleavage in the presence of $BBr_3$ can selectively turn the alkoxyl group (RO group) into a hydroxy group. The subsequent condensation reaction of the obtained 4-acylaralkylphenol expressed by general formula (6) and phenols expressed by general formula (4) above is similar to that used in process B1 mentioned above.

Also in process B3, the condensation reaction of the 4-acylaralkylphenylethers expressed by general formula (9) and phenols expressed by general formula (4) above may be similar to the method described in process B2 mentioned above.

Next in process C4, any known cleavage reaction relating to phenylether can be used. For example, implementing cleavage in the presence of HBr can turn the alkoxyl group (RO group) into a hydroxy group.

By sequentially implementing processes A2, C3 and B1 mentioned above (third producing method) or processes A2, B3 and C4 (fourth producing method) using 4-aralkylphenylethers expressed by general formula (2c) as the starting material, the target product of the present invention, or trisphenols expressed by general formula (1), can be obtained.

Also under the method for producing trisphenols expressed by general formula (1) from 4-acylaralkylphenol derivative expressed by general formula (3) where Xa is an organic sulfonyl group ($R'$—$SO_2$ group; $R'$ represents a hydrocarbon group), any known elimination reaction (decomposition reaction) relating to sulfonyloxy group can be used if 4-acylaralkylphenols expressed by general formula (6) are obtained by eliminating the Xa group in the 4-acylaralkylphenol derivative. If Xa is a tosyl group, for example, hydrolyzing it using alkali such as potassium carbonate, potassium hydroxide or the like turns the tosyloxy group into a hydroxyl group. If Xa is a mesyl group, cleavage reaction using phenylmagnesiumbromide or phenyllithium turns the mesyloxy group into a hydroxyl group. Next, the obtained 4-acylaralkylphenols expressed by general formula (6) are passed through process B1 mentioned above to obtain the target trisphenols. Or in the case of condensation reaction of 4-acylaralkylphenol derivative expressed by general formula (3) with phenols expressed by general formula (4), conditions similar to those used in the condensation reaction mentioned in connection with process B1 or B2 above may be used for the molar ratio of phenols and material compound, catalyst and its amount, use of co-catalyst, solvent and its amount, reaction temperature, reaction method, etc., and thereafter any known method mentioned above can be used to eliminate the sulfonyl group in the obtained trisphenol derivative expressed by general formula (5) to obtain the target trisphenols.

Example 1

Synthesis of 4-(1-(4-acetoxyphenyl)-1-methylethyl) acetophenone (Process A1b)

Into a 500-ml four-way flask fitted with a drip funnel, cooling tube and agitator, 70.5 g (0.542 mol) of aluminum chloride and 105.8 g (1.5 times by weight of aluminum chloride) of chloroform were introduced and the system was cooled to 5° C. while substituting the interior with nitrogen. After the cooling, 42.3 g (0.542 mol) of acetyl chloride was dripped from the drip funnel over a period of 1 hour to form a complex. The complex did not dissolve in chloroform at 5° C. and slurry solution was created in the system.

After the complex had been formed, a solution prepared by dissolving 50.0 g (0.236 mol) of p-cumylphenol in 75 g (1.5 times by weight of p-cumylphenol) of chloroform was dripped into the complex solution over a period of 3 hours by maintaining the temperature in the flask at 5° C. and, after the entire volume had been dripped, the mixture was caused to react at 20° C. for 2 hours.

When the reaction was complete, 171.8 g (0.5 time by weight of the content in the flask) of toluene was added to the liquid reaction mixture.

Next, 275.1 g of water was introduced into a 1-L four-way flask fitted with a reflux cooling tube and agitator, and the aforementioned toluene solution of liquid reaction mixture was dripped into this flask by maintaining the temperature in the flask at 40 to 50° C.

After the entire volume had been dripped, 103.1 g of 35% hydrochloric acid was added and the mixture was agitated for 1 hour at 30° C., after which the water layer was separated and removed. The obtained organic layer was neutralized by adding an aqueous solution of sodium hydroxide, after which the water layer was removed and then chloroform was distilled out at normal pressure.

Next, water was added to the obtained solution to wash it, and the water layer was separated and removed, and then 100 g of 16% aqueous solution of sodium hydroxide was added to the oil layer and the mixture was agitated for 1 hour for the purpose of washing, after which 75% phosphoric acid was added to neutralize the mixture and remove the water layer. The obtained oil layer was distilled to 10 kPa at 60° C. to remove toluene. Then, 73.9 g of toluene and 73.9 g of isooctane were added to the residue after distillation, after which the mixture was heated and dissolved, crystallized, cooled, filtered and dried to obtain 42.3 g of light yellowish white crystal with a purity of 97.3% based on high-performance liquid chromatography (hereinafter sometimes referred to as "HPLC"). When this crystal was analyzed by NMR and mass spectrometry, it was confirmed as 4-(1-(4-acetoxyphenyl)-1-methylethyl)acetophenone.

$^1$H-NMR (400 MHz, CDCl$_3$, standard substance: tetramethylsilane)

7.86 (aromatic H, 2H, double lines, J=8.78 Hz, b in the figure), 7.32 (aromatic H, 2H, double lines, J=8.78 Hz, c in the figure), 7.200 (aromatic H, 2H, double lines, J=8.78 Hz, e in the figure), 6.99 (aromatic H, 2H, double lines, J=8.78 Hz, f in the figure), 2.57 (CH$_3$CO—, 3H, single line, a in the figure), 2.28 (acetoxy, 3H, single line, g in the figure), 1.69 (methyl, 6H, single line, d in the figure)

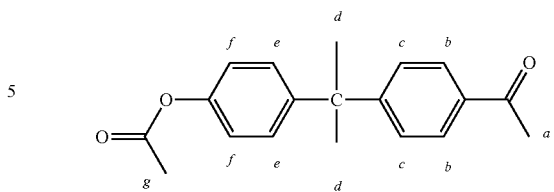

Example 2

Synthesis of 4-(1-(4-hydroxyphenyl)-1-methylethyl) acetophenone (Process C1)

From the crystal obtained in Example 1, 20.1 g was dissolved in 20 g of toluene, to which 24.0 g of 16% aqueous solution of sodium hydroxide and 2 g of methanol were added and the mixture was hydrolyzed for 2.5 hours at 50° C. When the reaction was complete, the mixture was neutralized by 75% phosphoric acid, after which the water layer was removed.

The obtained oil layer was distilled to 10 kPa at 60° C. to remove toluene, to obtain 18.0 g of orange solid with a purity of 99.9% based on HPLC.

When this solid was analyzed by NMR and mass spectrometry, it was confirmed as 4-(1-(4-hydroxyphenyl)-1-methylethyl)acetophenone.

The yield relative to p-cumylphenol was 60.0%.

$^1$H-NMR (400 MHz, CDCl$_3$, standard substance: tetramethylsilane)

7.86 (aromatic H, 2H, double lines, J=8.78 Hz, b in the figure), 7.32 (aromatic H, 2H, double lines, J=8.78 Hz, c in the figure), 7.07 (aromatic H, 2H, double lines, J=8.78 Hz, e in the figure), 6.76 (aromatic H, 2H, double lines, J=8.78 Hz, f in the figure), 5.95 (hydroxyl, 1H, broad single line, g in the figure), 2.57 (CH$_3$CO—, 3H, single line, a in the figure), 1.67 (methyl, 6H, single line, d in the figure)

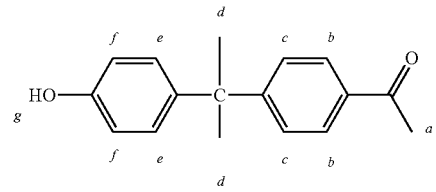

Example 3

Synthesis of 1-(α,α-bis(4-hydroxyphenyl)ethyl)-4-(α-methyl-α-(4-hydroxyphenyl)ethyl)benzene (Process B1)

Into a 300-ml four-way flask fitted with a drip funnel, cooling tube and agitator, 55.6 g of phenol and 1.7 g (3 percent by weight of phenol introduced) of toluene were introduced, after which dodecylmercaptan (12.5 percent by mol of material ketone) was introduced, and the system was heated to 40° C. while substituting the interior with nitrogen.

After having been substituted with nitrogen, the interior of the system was substituted with hydrogen chloride gas. While supplying hydrogen chloride gas, a solution prepared by dissolving 24.6 g (0.096 mol) of the 4-[1-methyl-1-(4-hydroxyphenyl)ethyl]acetophenone obtained by Example 2 in 24.6 g of phenol was dripped into the flask over a period of 3 hours while maintaining the temperature in the flask at 40 to 45° C.

After the entire volume had been dripped, the mixture was agitated for 18 hours at 40° C. to continue with the reaction. When the reaction was complete, 35.7 g of toluene was added to the reaction mixture, after which 16% aqueous solution of sodium hydroxide was added to neutralize the mixture, which was then heated to 87° C. to dissolve the crystal. This was followed by crystallization and cooling to 30° C., after which precipitated crystal was filtered out and dried to obtain 58.7 g of white crystal with a purity of 96.5% based on high-performance liquid chromatography (HPLC).

The obtained crystal was heated and dissolved in toluene, followed by crystallization. The crystallized solution was cooled and crystal was filtered out and dried to obtain 99.6% white crystal. When this crystal was analyzed by proton NMR and mass spectrometry, it was confirmed as the target, or 1-α-methyl-α,α-bis(4-hydroxyphenyl)ethyl)-4-(α-methyl-α-(4-hydroxyphenyl)ethyl)benzene.

Molecular weight: 423 (M-H)⁻ (liquid chromatography mass spectrometry)

$^1$H-NMR (400 MHz, CD$_3$OD, standard substance: tetramethylsilane) 7.01 to 7.05 (4H, m), 6.92 (2H, d, J=7.81 Hz), 6.85 (4H, d, J=7.81 Hz), 6.62 to 6.67 (6H, m), 4.85 (3H, brs), 2.01 (3H, s), 1.58 (6H, s)

Example 4

Synthesis of 4-(1-(4-hydroxyphenyl)-1-methylethyl)acetophenone (Process A1b+Process C1)

Into a 2-L four-way flask fitted with a drip funnel, cooling tube and agitator, 306.7 g (2.30 mol) of aluminum chloride and 460.0 g (1.5 times by weight of aluminum chloride) of chloroform were introduced and the system was cooled to 5° C. while substituting the interior with nitrogen. After the cooling, 117.4 g (1.15 mol) of acetic anhydride was dripped from the drip funnel over a period of 1 hour under agitation to form a complex. The complex did not dissolve in chloroform at 5° C. and therefore slurry solution was created.

Thereafter, a solution prepared by dissolving 106.0 g (0.50 mol) of p-cumylphenol in 159.1 g (1.5 times by weight of p-cumylphenol) of chloroform was dripped into the slurry solution over a period of 3 hours at 5° C. under agitation and, after the entire volume had been dripped, the mixture was caused to react at 5° C. for another 2 hours under agitation.

When the reaction was complete, 619.0 g of toluene was added to dilute the liquid reaction mixture. Next, 574.6 g of water was introduced into a 3-L four-way flask fitted with a cooling tube and agitator, and the aforementioned toluene-diluted reaction liquid was dripped into this water at 10 to 20° C. under agitation. After the entire volume had been dripped, 346.5 g of 35% hydrochloric acid was added and the mixture was agitated for 1 hour at 50° C. Thereafter, precipitated solids were filtered out and the water layer constituting the filtrate was separated and removed. After neutralizing the obtained oil layer by adding 16% aqueous solution of sodium hydroxide, 35% hydrochloric acid was added and the mixture was agitated for the purpose of washing, after which the water layer was separated and 16% aqueous solution of sodium hydroxide was added again to the obtained oil layer to neutralize the mixture. The water layer was separated and removed and the obtained oil layer was distilled to remove 419.5 g of solvent, and water was added to the obtained residual liquid after distillation and the mixture was agitated, and then the water layer was separated and removed. Next, 127.6 g of 16% aqueous solution of sodium hydroxide and 36.1 g of methanol were added to the obtained oil layer and the mixture was hydrolyzed for 2 hours at 50° C. under agitation. When the reaction was complete, 75% phosphoric acid was added to neutralize the mixture, and then the water layer was separated and removed and water was added to wash the oil layer, after which the water layer was separated and removed and the obtained oil layer was distilled at 70° C. under decompression to remove toluene. Then to the residula liquid after distillation, 56.1 g (0.5 time by weight of the residula liquid after distillation) of methylisobutylketone and 224.5 g (2 times by weight of residual liquid after distillation) of cyclohexane were added and the mixture was heated and dissolved, followed by crystallization, filtering and drying to obtain 65.7 g of white powder. When this crystal was analyzed by proton NMR and mass spectrometry, it was confirmed as 4-(1-(4-hydroxyphenyl)-1-methylethyl)acetophenone.

The yield relative to p-cumylphenol was 50.3%.

Example 5

Synthesis of 1-acetoxy-4-(1-methyl-1-phenylethyl)benzene (Process A1a, First Stage)

Into a 500-ml four-way flask fitted with a drip funnel, cooling tube and agitator, 100 g (0.471 mol) of p-cumylphenol, 50.0 g (0.832 mol) of glacial acetic acid and 0.6 g (0.832 mol) of 75% phosphoric acid were introduced and the system was heated to a range of 90 to 95° C. while substituting the interior with nitrogen. After the heating, 57.7 g (0.565 mol) of acetic anhydride was dripped over a period of 1 hour while maintaining the internal temperature at 90 to 95° C. to cause reaction. After the dripping, the mixture was agitated for 3 hours at the same temperature to cause reaction. When the reaction was complete, acetic acid was removed by distillation under decompression, and 200 g of cyclohexane was added to dissolve the residue after distillation. Next, 10% aqueous solution of sodium carbonate was added to this solution and the mixture was agitated, after which the water layer was separated and removed. Then, 10% aqueous solution of sodium carbonate was added to the obtained organic layer, followed by washing and removal of the water layer using similar operations.

Distilled water was added further to the obtained organic layer and the mixture was agitated, after which the water layer was separated and removed. Similarly, water was added to the obtained oil layer for the purpose of water washing, followed by removal of the water layer, and this operation was performed twice. Cyclohexane was distilled out from the obtained organic layer, to obtain colorless, clear liquid with a purity of 98.2% based on gas chromatography.

When this liquid was analyzed by NMR and mass spectrometry, it was confirmed as 1-acetoxy-4-(1-methyl-1-phenylethyl)benzene.

The yield relative to p-cumylphenol was 98.4%.

Molecular weight: 254 (gas chromatography mass spectrometry)

1H-NMR (400 MHz, CDCl$_3$, standard substance: tetramethylsilane)

1.67 (6H, s), 2.27 (3H, s), 6.96 to 6.98 (2H, m), 7.17 to 7.26 (7H, m)

Example 6

Synthesis of 4-[1-(4-acetoxyphenyl)-1-methylethyl]acetophenone (Process A1a, second stage)

Into a 1-L four-way flask fitted with a drip funnel, cooling tube and agitator, 98.1 g (0.736 mol) of aluminum chloride and 147.2 g of dichloromethane were introduced and the system was cooled to 5° C. while substituting the interior with nitrogen. After the cooling, 37.6 g (0.368 mol) of acetic anhydride was dripped over a period of 1.5 hours while maintaining the temperature at 5 to 10° C. to form a complex.

After the complex had formed, a solution prepared by dissolving 76.3 g (0.30 mol) of the 1-acetoxy-4-(1-methyl-1-phenylethyl)benzene obtained by Example 5 in 114.5 g of dichloromethane was dripped into the complex solution over a period of 3 hours while maintaining the internal temperature at 5 to 10° C. and, after the entire volume had been dripped, the mixture was caused to react at 5° C. for 1.5 hours. When the reaction was complete, 400 g of toluene was added to the liquid reaction mixture.

Next, 250.0 g of distilled water was introduced into a 2-L four-way flask fitted with a reflux cooling tube and agitator, and the aforementioned toluene solution of liquid reaction mixture was dripped into this flask.

After the entire volume had been dripped, 93.4 g of 25% hydrochloric acid was added to the organic layer obtained by separating and removing the water layer, and the mixture was agitated for 30 minutes at 30° C., after which the water layer was separated and removed. Next, 93.4 g of 25% hydrochloric acid was added to the obtained organic layer, followed by washing and removal of the water layer using similar operations. Aqueous solution of sodium hydroxide was added to the obtained organic layer to neutralize the layer, after which the water layer was separated and removed and then distilled water was added to the organic layer, and the mixture was agitated, after which the water layer was separated and removed. Distilled water was added to the organic layer, followed by washing and removal of the water layer using similar operations.

Thereafter, solvent was distilled out from the obtained organic layer under decompression.

Next, 45.5 g of methylisobutylketone and 135.6 g of cyclohexane were added to the residue after distillation, followed by cooling and crystallization. Precipitated crystal was filtered out and dried to obtain 19.5 g of white crystal, or 4-[1-(4-acetoxyphenyl)-1-methylethyl]acetophenone, with a purity of 97.6% based on gas chromatography.

Example 7

Synthesis of 1-[α,α-bis(4-hydroxyphenyl)ethyl]-4-[α-methyl-α-(4-hydroxyphenyl)ethyl]benzene Into a 200-ml four-way flask fitted with a drip funnel, cooling tube and agitator, 22.6 g (0.240 mol) of phenol, 0.7 g (3 percent by weight of phenol introduced) of toluene and 0.5 ml of dodecyl mercaptan were introduced and the system was heated to 45° C. while substituting the interior with nitrogen.

After having been substituted with nitrogen, the interior of the system was substituted with hydrogen chloride gas. A solution prepared by dissolving 11.2 g (0.038 mol) of the 4-[1-(4-acetoxyphenyl)-1-methylethyl]acetophenone obtained by Example 6 in 11.2 g (0.119 mol) of phenol was dripped into the flask over a period of 1.5 hours while maintaining the temperature in the flask at 45° C. Supply of hydrochloric acid gas into the system was continued while dripping. When the entire volume had been dripped, the mixture was agitated for 21 hours at 50° C. to continue with the reaction. When the reaction was complete, 50.0 g of toluene and 10.0 g of distilled water were added to the reaction mixture, after which 16% aqueous solution of sodium hydroxide was added to neutralize the mixture, which was then heated to 85° C. to dissolve the crystal and the water layer was separated and removed. Distilled water was added to the obtained organic layer for the purpose of washing with water, followed by separation and removal of the water layer, and this operation was performed twice. The obtained organic layer was crystallized and precipitated crystal was filtered out and dried to obtain 13.6 g of white crystal, or 1-[α,α-bis(4-hydroxyphenyl)ethyl]-4-[α-methyl-α-(4-hydroxyphenyl)ethyl]benzene, with a purity of 95.5% based on high-performance liquid chromatography.

The yield relative to 4-(1-(4-acetoxyphenyl)-1-methylethyl)acetophenone was 83.2%.

What is claimed is:

1. A method for producing trisphenols expressed by general formula (1)

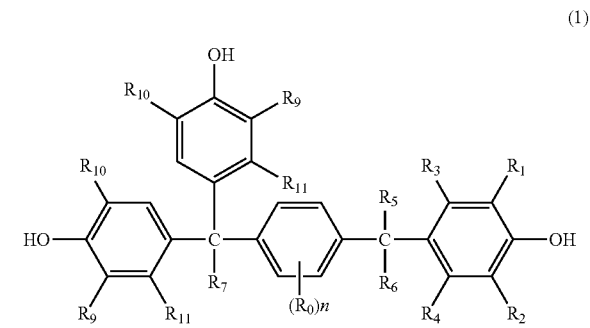

(1)

(wherein $R_1$ to $R_4$ each independently represent a hydrogen atom, alkyl group, alkoxyl group, aromatic hydrocarbon group, halogen atom, acyloxy group or hydroxyl group; $R_5$ and $R_6$ each independently represent a hydrogen atom or alkyl group; $R_7$ represents a hydrogen atom or alkyl group; $R_0$ represents an alkyl group, alkoxyl group or halogen atom; n is 0 or an integer of 1 to 4, where if n is 2 or greater, all $R_0$'s may be the same or different; and $R_9$ to $R_{11}$ each independently represent a hydrogen atom, alkyl group, alkoxyl group, aromatic hydrocarbon group, halogen atom or hydroxyl group), said producing method characterized by using as a starting material 4-aralkylphenol derivatives expressed by general formula (2)

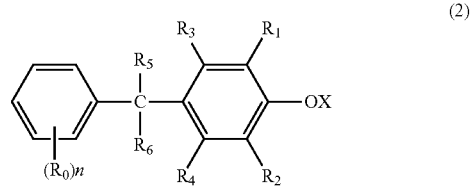

(2)

(wherein $R_1$ to $R_4$, $R_5$ and $R_6$, and $R_0$ and n are the same as the corresponding items in general formula (1), while X represents a hydrogen atom or leaving group that can be substituted with a hydrogen atom, where if n is 1 or greater, $R_0$ is not substituted at the 4-position of the phenyl group).

2. A method for producing trisphenols according to claim 1, wherein the leaving group that can be substituted with a hydrogen atom, expressed by X in general formula (2), is an acyl group.

3. A method for producing trisphenols according to claim 1, characterized by comprising a nucleus-acylation process (A) as well as subsequent phenols condensation process (B) and elimination process (C) for substituting Xa with a hydrogen atom:

Process (A): Nucleus-acylate 4-aralkylphenol derivatives expressed by general formula (2) above to obtain 4-acylaralkylphenol derivatives expressed by general formula (3)

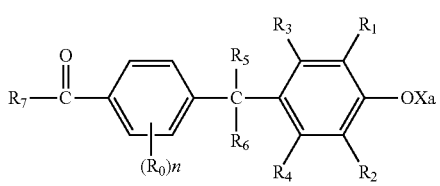

(3)

(wherein $R_1$ to $R_4$, $R_5$ and $R_6$, and $R_0$ and n are the same as the corresponding items in general formula (2), while $R_7$ is the same as the corresponding item in general formula (1) and Xa represents a leaving group that can be substituted with a hydrogen atom);

Process (B): Cause phenols expressed by general formula (4)

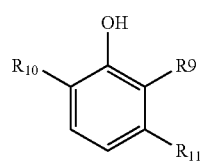

(4)

(wherein $R_9$ to $R_{11}$ are the same as the corresponding items in general formula (1))

to undergo condensation reaction with the 4-acylaralkylphenol derivatives expressed by general formula (3) above as obtained by process (A), to obtain trisphenol derivatives expressed by general formula (5)

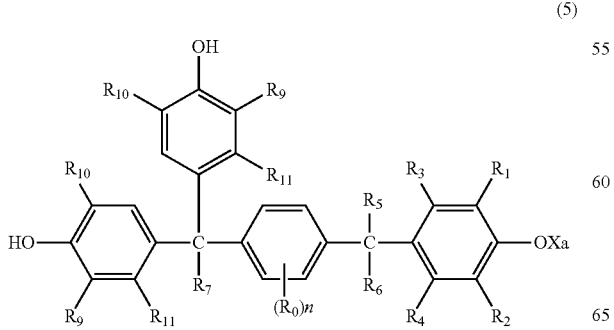

(5)

(wherein $R_1$ to $R_4$, $R_5$ and $R_6$, $R_0$ and n, $R_7$, and $R_9$ to $R_{11}$ are the same as the corresponding items in general formula (1), while Xa represents a leaving group that can be substituted with a hydrogen atom)

or, cause the phenols expressed by general formula (4) to undergo condensation reaction with the 4-acylaralkylphenols expressed by general formula (6) as obtained by process (C), to obtain trisphenols expressed by general formula (1); and Process (C): Eliminate the Xa group of the 4-acylaralkylphenol derivatives expressed by general formula (3) as obtained by process (A), to obtain 4-acylaralkylphenols expressed by general formula (6)

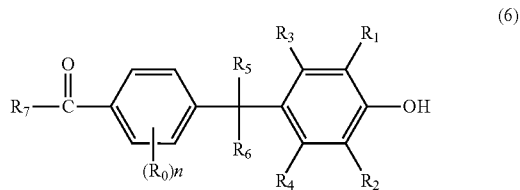

(6)

(wherein $R_1$ to $R_4$, $R_5$ and $R_6$, $R_0$ and n, and $R_7$ are the same as the corresponding items in general formula (1))

or, eliminate the Xa group of the trisphenol derivatives expressed by general formula (5) as obtained by process (B), to obtain trisphenols expressed by general formula (1).

4. A method for producing trisphenols according to claim 1, wherein when general formula (2) above is expressed as general formula (2a) where X is an acyl group, or as general formula (2b) where X is a hydrogen atom, said producing method comprising processes A1, C1 and B1 in this sequence (first producing method) or processes A1, B2 and C2 in this sequence (second producing method):

Process A1: Nucleus-acylate 4-aralkylphenylesters expressed by general formula (2a)

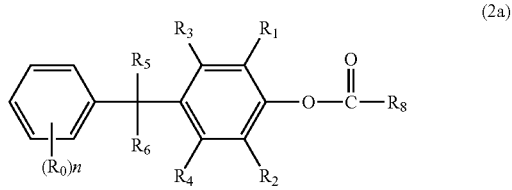

(2a)

(wherein $R_1$ to $R_4$, $R_5$ and $R_6$, and $R_0$ and n are the same as the corresponding items in general formula (2), while $R_8$ represents a hydrogen atom or hydrocarbon group, where if n is 1 or greater, $R_0$ is not substituted at the 4-position of the phenyl group)

or, 4-aralkylphenols expressed by general formula (2b)

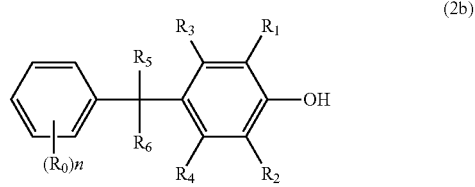

(2b)

(wherein $R_1$ to $R_4$, $R_5$ and $R_6$, and $R_0$ and n are the same as the corresponding items in general formula (2), where if n is 1 or greater, $R_0$ is not substituted at the 4-position of the phenyl group)
to obtain 4-acylaralkylphenylesters expressed by general formula (7)

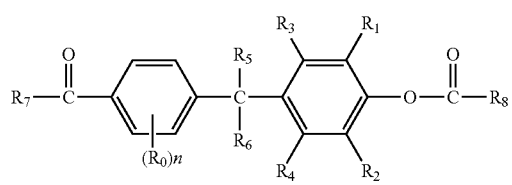

(7)

(wherein $R_1$ to $R_4$, $R_5$ and $R_6$, $R_0$ and n, and $R_7$ are the same as the corresponding items in general formula (1), while $R_8$ is the same as the corresponding item in general formula (2a));

Process C1: Hydrolyze, alcoholyze or phenolyze the ester group of the 4-acylaralkylphenylesters expressed by general formula (7), to obtain 4-acylaralkylphenols expressed by general formula (6)

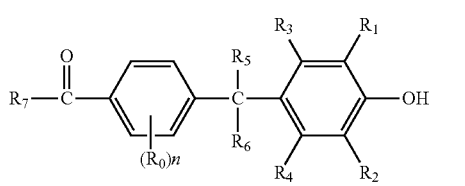

(6)

(wherein $R_1$ to $R_4$, $R_5$ and $R_6$, $R_0$ and n, and $R_7$ are the same as the corresponding items in general formula (1));

Process B1: Next, cause the obtained 4-acylaralkylphenols to undergo condensation reaction with phenols expressed by general formula (4)

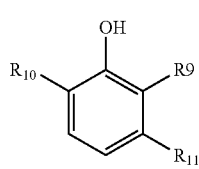

(4)

(wherein $R_9$ to $R_{11}$ are the same as the corresponding items in general formula (1))
to obtain trisphenols expressed by general formula (1);

Process B2: Cause 4-acylaralkylphenylesters expressed by general formula (7) to undergo condensation reaction with phenols expressed by general formula (4), to obtain monoester-substituted trisphenols expressed by general formula (8)

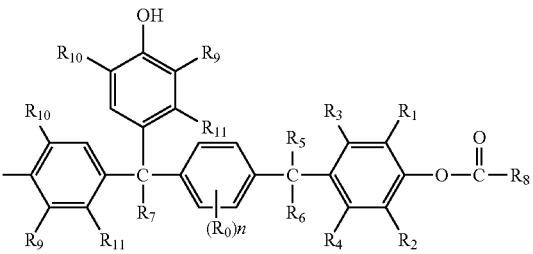

(8)

(wherein $R_1$ to $R_4$, $R_5$ and $R_6$, $R_0$ and n, $R_7$, and $R_9$ to $R_{11}$ are the same as the corresponding items in general formula (1), while $R_8$ is the same as the corresponding item in general formula (2a)); and Process C2: Next, hydrolyze, alcoholyze or phenolyze the ester group of the obtained monoester-substituted trisphenols, to obtain trisphenols expressed by general formula (1).

5. A method for producing trisphenols according to claim 4, wherein the condensation reaction with phenols is implemented along with the hydrolysis reaction, alcoholysis reaction and/or phenolysis reaction in a same process.

6. A method for producing trisphenol compounds expressed by general formula (5)

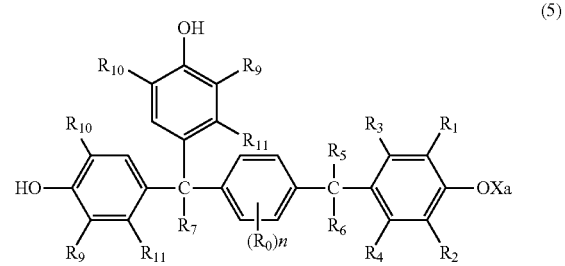

(5)

(wherein $R_1$ to $R_4$ each independently represent a hydrogen atom, alkyl group, alkoxyl group, aromatic hydrocarbon group, halogen atom, acyloxy group or hydroxyl group; $R_5$ and $R_6$ each independently represent a hydrogen atom or alkyl group; $R_7$ represents a hydrogen atom or alkyl group; $R_0$ represents an alkyl group, alkoxyl group or halogen atom; n is 0 or an integer of 1 to 4, where if n is 2 or greater, all $R_0$'s may be the same or different; and $R_9$ to $R_{11}$ each independently represent a hydrogen atom, alkyl group, alkoxyl group, aromatic hydrocarbon group, halogen atom or hydroxyl group; Xa represents a leaving group that can be substituted with a hydrogen atom), said method comprising:

Process (A): Nucleus-acylate 4-aralkylphenol compounds expressed by general formula (2) to obtain 4-acylaralkylphenol compounds expressed by general formula (3)

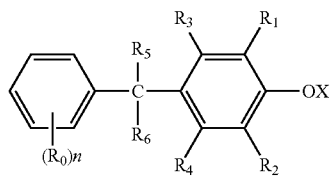

(2)

(wherein $R_1$ to $R_4$, $R_5$ and $R_6$, and $R_0$ and n are the same as the corresponding items in general formula (5), while X represents a hydrogen atom or leaving group that can be substituted with a hydrogen atom, where if n is 1 or greater, $R_0$ is not substituted at the 4-position of the phenyl group);

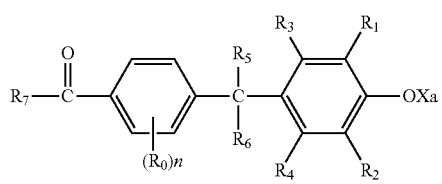

(3)

(wherein $R_1$ to $R_4$, $R_5$ and $R_6$, and $R_0$ and n are the same as the corresponding items in general formula (2), while $R_7$ and Xa are the same as the corresponding items in general formula (5)); and Process (B): Cause phenols expressed by general formula (4)

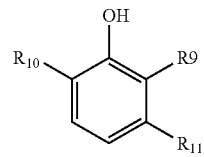

(4)

(wherein $R_9$ to $R_{11}$ are the same as the corresponding items in general formula (5))

to undergo condensation reaction with the 4-acylaralkylphenol compounds expressed by general formula (3) above as obtained by process (A), to obtain the trisphenol compounds expressed by general formula (5).

\* \* \* \* \*